(12) United States Patent
Kaintz et al.

(10) Patent No.: US 9,039,592 B2
(45) Date of Patent: May 26, 2015

(54) RADIOPHARMACEUTICAL DELIVERY DEVICE

(71) Applicant: MEDRAD, INC., Indianola, PA (US)

(72) Inventors: Ryan Kaintz, Allison Park, PA (US); Jason L. Bazala, Irwin, PA (US); Douglas DeScalzi, Pittsburgh, PA (US); Scott R. Griffith, Murrysville, PA (US); Bruno Fazi, Pittsburgh, PA (US); Charles Marsh, Cranberry Township, PA (US); James A. Agamaite, Wexford, PA (US); Matthew Sass, Pittsburgh, PA (US); Carl Michael Benson, Pittsburgh, PA (US); Matthew Beale, Pittsburgh, PA (US); Courtney N. Southard, Sewickley, PA (US)

(73) Assignee: Bayer Medical Care Inc., Indianola, PA (US)

( * ) Notice: Subject to any disclaimer, the term of this patent is extended or adjusted under 35 U.S.C. 154(b) by 0 days.

(21) Appl. No.: 13/828,987

(22) Filed: Mar. 14, 2013

(65) Prior Publication Data
US 2013/0331634 A1   Dec. 12, 2013

Related U.S. Application Data

(60) Provisional application No. 61/656,716, filed on Jun. 7, 2012.

(51) Int. Cl.
*A61N 5/00* (2006.01)
*A61M 39/22* (2006.01)

(52) U.S. Cl.
CPC .................................. *A61M 39/223* (2013.01)

(58) Field of Classification Search
USPC ............................. 600/1–8; 604/131, 258, 284
See application file for complete search history.

(56) References Cited

U.S. PATENT DOCUMENTS

| | | | |
|---|---|---|---|
| 4,401,108 A | 8/1983 | Galkin et al. | |
| 4,409,966 A | 10/1983 | Lambrecht et al. | |

(Continued)

FOREIGN PATENT DOCUMENTS

| | | |
|---|---|---|
| IT | MA96A000148 | 3/1996 |
| WO | 0137904 A2 | 5/2001 |

OTHER PUBLICATIONS

The International Preliminary Report on Patentability mailed Jun. 11, 2014 from corresponding PCT Application No. PCT/US2013/044038.

*Primary Examiner* — John Lacyk
(74) *Attorney, Agent, or Firm* — Joseph L. Kent; David Schramm; James R. Stevenson

(57) ABSTRACT

A device for delivery of a radiopharmaceutical and, in some embodiments, delivery of a pharmaceutical agent are provided herein. A fluid path set comprising a confluence valve, a four-way valve, and one or more tubing sections which are designed to place some combination of a radiopharmaceutical source, a medical fluid source, and a pharmaceutical agent source in sterile fluid communication with a patient or a waste receptacle. Also provided are holders for the fluid path set, and a sterile fluid delivery kit comprising the holder and fluid path set. A fluid delivery system may accept the holder with the fluid path set installed and various sources of radiopharmaceuticals, pharmaceuticals, and medical fluids. The fluid delivery system allows for automated mixing and delivery of exact amounts of these agents to a patient while improving efficiency and safety, and reducing waste.

24 Claims, 45 Drawing Sheets

(56) References Cited

U.S. PATENT DOCUMENTS

| | | | | |
|---|---|---|---|---|
| 4,472,403 | A | 9/1984 | Trijzelaar et al. | |
| 4,562,829 | A | 1/1986 | Bergner | |
| 4,585,009 | A | 4/1986 | Barker et al. | |
| 4,883,459 | A | 11/1989 | Calderon | |
| 4,902,282 | A * | 2/1990 | Bellotti et al. | 604/258 |
| 5,383,858 | A | 1/1995 | Reilly et al. | |
| 5,472,403 | A | 12/1995 | Cornacchia et al. | |
| 5,514,071 | A | 5/1996 | Sielaff, Jr. et al. | |
| 5,520,653 | A | 5/1996 | Reilly et al. | |
| 5,918,443 | A | 7/1999 | Phillips | |
| 5,927,351 | A | 7/1999 | Zhu et al. | |
| 5,947,890 | A | 9/1999 | Spencer et al. | |
| 6,267,717 | B1 | 7/2001 | Stoll et al. | |
| 6,450,936 | B1 | 9/2002 | Smith, III et al. | |
| 6,471,674 | B1 | 10/2002 | Emig et al. | |
| 6,520,930 | B2 | 2/2003 | Critchlow et al. | |
| 6,767,319 | B2 | 7/2004 | Reilly et al. | |
| 7,018,363 | B2 | 3/2006 | Cowan et al. | |
| 7,204,797 | B2 | 4/2007 | Reilly et al. | |
| 7,905,861 | B2 | 3/2011 | Rhinehart et al. | |
| 8,198,599 | B2 | 6/2012 | Bouton et al. | |
| 2003/0040700 | A1 * | 2/2003 | Hickle et al. | 604/67 |
| 2008/0177126 | A1 * | 7/2008 | Tate et al. | 600/5 |
| 2010/0063481 | A1 | 3/2010 | Hoffman et al. | |
| 2011/0021905 | A1 * | 1/2011 | Patrick et al. | 600/424 |
| 2011/0178359 | A1 | 7/2011 | Hirschmann et al. | |

* cited by examiner

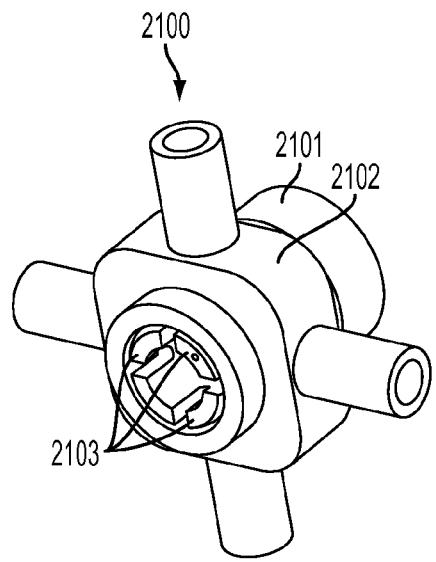
FIG. 2C-I
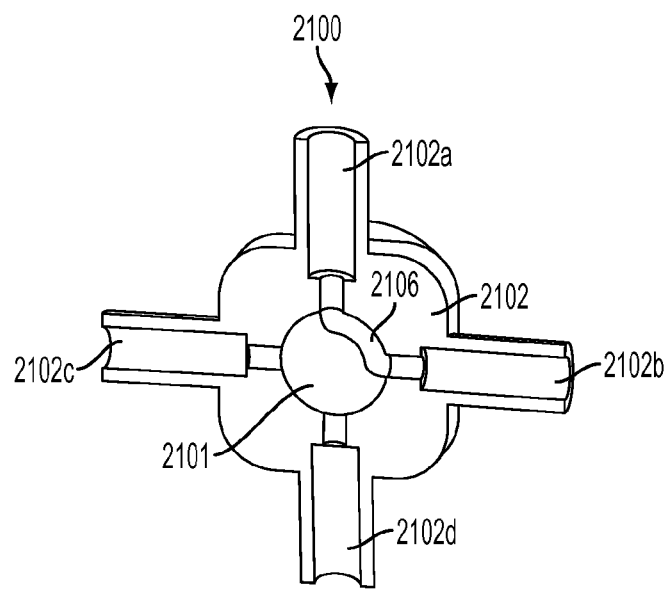
FIG. 2C-II

FIG. 39

RADIOPHARMACEUTICAL DELIVERY DEVICE

CROSS-REFERENCE TO RELATED APPLICATIONS

This application claims priority to U.S. Provisional No. 61/656,716 filed Jun. 7, 2012, entitled "Radiopharmacuetical Delivery Device" the contents of which are hereby incorporated by reference in their entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISK

Not applicable

BACKGROUND

Contrast agents are provided by manufacturers in numerous concentrations in sterilized containers (such as glass bottles or plastic packages) ranging incrementally in size from 20 ml to 200 ml. These containers are generally designed for a single use in which once a container is opened for a patient, then it is used for that patient only. The contrast is, generally, aspirated from such containers via a syringe pump used to inject the contrast agent, and any contrast agent remaining in the container is discarded to prevent infection with potentially contaminated contrast. The medical staff is faced with the task of choosing an appropriately sized contrast container to assure an adequate injection while minimizing discarded contrast. Time consuming procedures are required to reload the syringe if more contrast is required than originally calculated, and expensive waste results if only a portion of a filled syringe is injected. The inventory of contrast containers required under the current system increases costs and regulatory burdens throughout the contrast media supplier-consumer chain.

SUMMARY OF THE INVENTION

Various embodiments are directed to a fluid delivery device including a confluence valve, a four-way valve, a first tubing section in fluid communication with a first input and the confluence valve, a second tubing section in fluid communication with a second input and the confluence valve, a third tubing section in fluid communication with the confluence valve and the four-way valve, an output tubing section in fluid communication with the four-way valve and at least one output fitting, a waste tubing section in fluid communication with the four-way valve and at least one waste receptacle, an auxiliary tubing section in fluid communication with the four-way valve and the confluence valve, and one or more pumps operably connected to the fluid path. In particular embodiments, the first input and the confluence valve, the second tubing section in fluid communication with the second input and the confluence valve, the third tubing section in fluid communication with the confluence valve and the four-way valve, the output tubing section in fluid communication with the four-way valve and at least one output fitting, the waste tubing section in fluid communication with the four-way valve and at least one waste receptacle, the auxiliary tubing section in fluid communication with the four-way valve and the confluence valve may be provided in a fluid path set. In some embodiments, these tubing sections and valves may be pre-connected and configured to be placed within the device by a user. In particular embodiments, the device or the fluid path may include a holder configured to hold a separate the components of the fluid path operably coupled to the fluid path.

In certain embodiments, the fluid path may include a coil assembly disposed between the confluence valve and the four way valve in fluid communication with at least the third tubing section. In some embodiments, the device may include well configured to accept the coil assembly, and one or more radiation detectors may be associated with the well. These radiation detectors can be any type of radiation detector including, for example, ionization chambers, CZT crystal detectors, Geiger-Muller counters, scintillating counters, parabolic detectors, and combinations thereof.

In some embodiments, at least one of the one or more pumps may be operably connected to the first tubing section, the second tubing section, or a combination thereof. In some embodiments, a medical fluid storage container may be coupled to the first input, and in certain embodiments, the medical fluid storage container may be a cylindrical device having a plunger slidably inserted into the fluid storage container creating a seal and a motor operably associated with the plunger. In particular embodiments, a fluid reservoir may be in fluid communication with the medical fluid storage container.

In some embodiments, a vial spike may be coupled to the second input, and in particular embodiments, a pharmaceutical vial coupled to the second input or reversibly coupled to the second input. The pharmaceutical vial of some embodiments may include a radiopharmaceutical.

In some embodiments, a pharmaceutical delivery port may be in fluid communication with the output tubing section, and in particular embodiments, a pharmaceutical delivery device may be operably connected with the pharmaceutical delivery port.

In certain embodiments, the a control system operably connected to the one or more pumps, and the control system may be at least capable of individually operating each of the one or more pumps. In some embodiments, the device may include a graphical user interface operably connected to the control system.

In particular embodiments, the device may include a body, and in some embodiments, the body may include troughs and wells configured to accommodate the fluid path. In certain embodiments, a holder configured to hold a separate the components of the fluid path in position to be inserted into the troughs and wells of the body may be operably coupled to the fluid path. In some embodiments, at least a portion of the body may include radioactive shielding. In some embodiments, a lid attached to the body, and the lid may be pivotably attached to the body. In certain embodiments, the first input, the second input, the output fitting or combinations thereof may include a swabable valve.

Certain embodiments are directed to a fluid path set including a confluence valve, a four-way valve, a first tubing section in fluid communication with a first input and the confluence valve, a second tubing section in fluid communication with a second input and the confluence valve, a third tubing section in fluid communication with the confluence valve and the four-way valve, an output tubing section in fluid communication with the four-way valve and at least one output fitting, a waste tubing section in fluid communication with the four-way valve and at least one waste receptacle, and an auxiliary tubing section in fluid communication with the four-way valve and the confluence valve. In particular embodiments, each of the first tubing section, second tubing section a third tubing section, output tubing section, a waste tubing section, and the auxiliary tubing section may be permanently attached to the confluence valve and four-way valve. In some embodiments, the fluid path set may further include a coil assembly disposed between the confluence valve and the four way valve in fluid communication with at least the third tubing section. In certain embodiments, the fluid path set may include a medical fluid storage container coupled to the first input, and the medical fluid storage container may include a cylindrical device having a plunger slidably inserted into the fluid storage container creating a seal. In some embodiments, the fluid path set may include a connector configured to connect to a fluid reservoir in fluid communication with the fluid storage container.

In some embodiments, the second input may include a vial spike. In other embodiments, the fluid path set may include a pharmaceutical delivery port in fluid communication with the output tubing section. In certain embodiments, the at least one waste receptacle may include an IV bag. The fluid path set of such embodiments may include various joints, linear joints, T-joints, 4-way joints, valves, check valves, by-pass valves, stop cocks, linkers, luer linkers, screw-type linkers, pressure fittings, and the like and combinations thereof. In some embodiments, the first input, the second input, the output fitting, or combinations thereof may include a swabable valve. In certain embodiments, the fluid path set may further include a holder operably coupled to the fluid path configured to hold a separate the components of the fluid path, and in some embodiments, the holder may be composed of a rigid material. In particular embodiments, the holder may include one or more grooves designed an configured to accept one or more of the first tubing section, second tubing section a third tubing section, output tubing section, a waste tubing section, and the auxiliary tubing section. In some embodiments, the holder may include one or more openings. In some embodiments, the holder may include a vial spike permanently attached to a portion of the holder.

DESCRIPTION OF DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

FIG. 2C is a drawing of a four-way valve.

FIG. 17 is screen shot representing an exemplary dosing protocol dose delivery input screen.

FIG. 22 is screen shot representing an exemplary dosing delivery input screen before test injection.

FIG. 23 is screen shot representing an exemplary dosing delivery input screen during saline test injection.

FIG. 27 is screen shot representing an exemplary dosing delivery input screen indicating progress of the dosing protocol.

FIG. 29 is screen shot representing an exemplary dosing delivery input screen upon completion of dose injection and transitioning to the radiopharmaceutical injection.

FIG. 30 is screen shot representing an exemplary dosing delivery input screen prior to injection of the radiopharmaceutical.

FIG. 36 is screen shot representing an exemplary window showing a patient schedule.

FIG. 39 is screen shot representing an exemplary pop-up window for providing parameters for a selected component.

DETAILED DESCRIPTION

Figure 1:
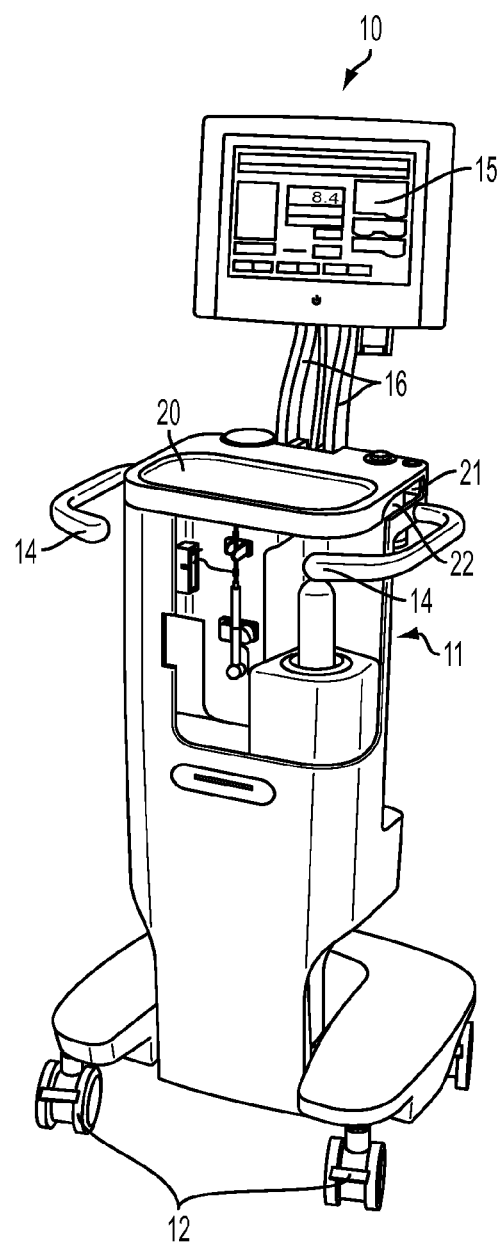
FIG. 1 is a drawing showing external features of the radiopharmaceutical delivery system of some exemplary embodiments.

The above summary of the present invention is not intended to describe each illustrated embodiment or every possible implementation of the present invention. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

FIG. 1 shows an exemplary embodiment of a radiopharmaceutical fluid delivery system 10. The fluid delivery system 10 may include a body 11 configured to house various components of the system in a confined area and wheels and/or casters 12 fixed to the body and being positioned to allow the system to be moved in one or more directions. In various embodiments, one or more of the wheels 12 may be lockable to prevent the system 10 from moving once it is in position. In some embodiments, the system 10 may include one or more handles 14 fixed to the body 11 and positioned to allow an operator to grasp the handle and move or position the system 10. In other embodiments, the fluid delivery system 10 may be a stand-alone or fixed-position apparatus, and in such embodiments, the fluid delivery system may not include wheels or casters or the wheels or casters may be movably concealed in the body 11. Such stand-alone or fixed position apparatuses may also not include handles or handles may be movably concealed in the body 11.

The fluid delivery system 10 generally includes a display or graphical user interface ("GUI") 15 attached to the body 11, and positioned to allow a user to view the display 15. In some embodiments, the display 15 may be immovably fixed to the body, and in other embodiments, the display 15 may be positioned away from the system 10 and attached to the system 10 by a hard wired or wireless network. In other embodiments, the display 15 may be pivotally connected to the body 11, by means of one or more movable arm 16 that is pivotally connected to a joint on the display 15 and/or a joint on the body 11. Such display 15 may be configured to be tilted or swiveled with respect to the arm 16 to allow the display 15 to be positioned by an operator.

The display 15 may be a color display, a black and white display, or a green-screen display, and in various embodiments, the display 15 may display real-time data with regard to the operation of the system 10. In some embodiments, the display 15 may be configured to allow a user to program or otherwise operate the system 10. For example, in certain embodiments, the display 15 may have touch-screen capabilities or be otherwise configured to allow a user to interact with the system 10, and in particular, the computer portion of the system 10, by manipulating or touching the display 15. In other embodiments, the system 10 may include a keyboard, mouse, microphone, hand switch, footswitch, or other device configured to allow the user to program or otherwise operate the system 10. In still other embodiments, the display 15 may be included as part of a laptop or tablet computer that is electronically associated to the system 10 by a hard wired or wireless network.

The body 11 may include a retractable lid or cover 20 having a primary handle 21 including a latch release 22, and in some embodiments, the lid or cover 20 may include a secondary handle (not shown). In some embodiments, the lid 20 may include a locking mechanism, such as a combination or a key lock (not shown) that is capable of interacting with the body 11 to lock the lid 20 in a closed position to prevent access of the system 10. In other embodiments, the locking mechanism may be a software-implemented lock, such as a password-protected access point, that is accessible through the display 15 and is adapted to lock the cover 20 in a closed position and/or to prevent access or operation of the system 10.

Figure 2A:
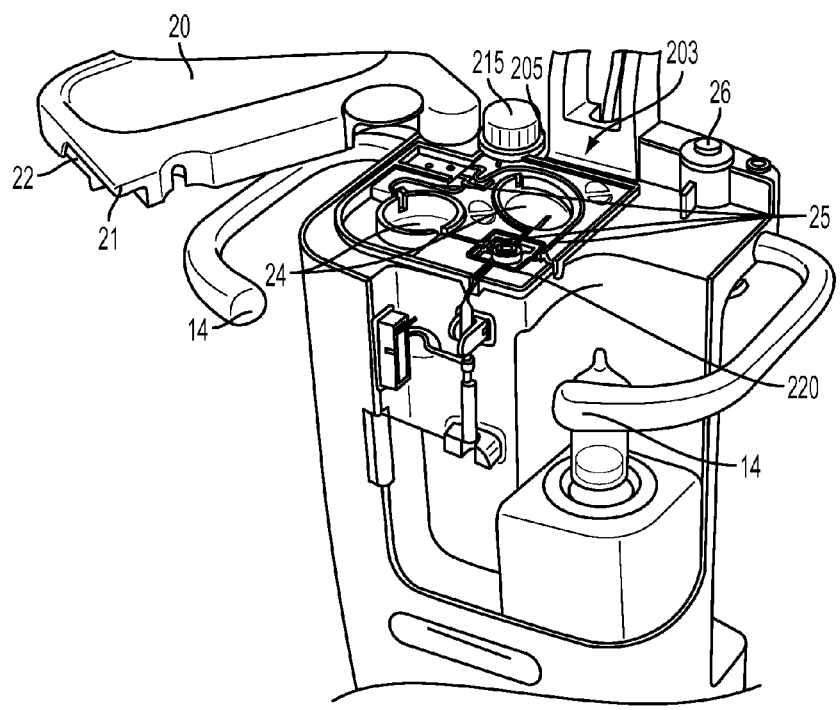
FIG. 2A is a drawing showing features of the troughs and wells configured to accommodate the fluid path set of the radiopharmaceutical delivery system of some exemplary embodiments.

As illustrated in FIG. 2A, the lid 20 may be movably attached to the body 11 at an upper portion of the body 11 and may cover an upper surface 203 that defines a number of recessed portions including, for example, wells 24 into which a vial or container of a pharmaceutical or a radiopharmaceutical and troughs 25 into which various components of a fluid path set (not shown) can be positioned during an injection procedure. The lid 20 may be reversibly moved with respect to the body 11 to allow access to the recessed portions of the body, and the lid 20 may be configured to allow for insertion and removal of vials or containers that may be positioned within the wells 24 and a fluid path set. In this manner, the radiopharmaceutical vial and the components of the fluid path set can lie below the plane of upper surface 203 of the body and can be completely covered by the lid 20. In other embodiments, a drawer type mechanism may be used that slidably displaces a surface having recessed portions into and out of the body 11.

In some embodiments, the system 10 may include an interrupt button 26 in FIG. 2A that is configured to allow an operator to pause or abort an injection procedure in the event of, for example, patient discomfort or an emergency, while by-passing the display 15, which also can be configured to allow the user to pause or abort an injection procedure. The interrupt button 26 may be connected to LEDs and/or a printed circuit board to provide visual and/or auditory alarms when the interrupt button 26 has been activated.

In some embodiments, the lid 20, upper surface 203, and various other portions of the body 11 may include suitable radioactive shielding (such as lead) for minimizing potential radiation exposure from the radiopharmaceutical to the operator. The upper surface 203 or one or more portions thereof can be covered by the lid 20 during use to limit radiation exposure to the operator, other medical personnel, patient, and other observers. In particular embodiments, the lid 20 may be configured to be operated using one hand. For example, in certain exemplary embodiments, the lid 20 may be attached to the body 11 by a pivot that allows the door to easily pivot away from the work surface of the body 11 during set-up and pivot back over the work surface during operation. The pivot hinge of such embodiments may be position away from the work surface sufficiently such that when the lid 20 is pivoted away from the work surface, the entire work surface is exposed. Therefore, the user can have access to any part of the system 10 during set-up. The lid 20 may then pivot back to cover the entire work surface thereby shielding the user during operation of the system 10. Single hand operation may be achieved by positioning a handle and locking mechanism at a position in which the operator can unlock and pivot the door with one hand. In certain embodiments, a motor may be used to assist the user in pivoting the door.

The recesses or troughs 25 of the upper surface 203 of the body may be configured to removably accept the components of the fluid path set, and place the fluid path set in position to connect the wells 24, pumps, and so forth required for the fluid delivery system 10. The wells 24 and troughs 25, and the fluid path described thereby, may be configured in any way to accommodate the necessary fluid path set.

The wells 24 and recesses or troughs 25 formed in the upper surface 203 can be sized, configured, or arranged to accommodate any length, design, or configuration of the fluid path set and the various components of the fluid path set 32 including pumps, medical fluid containers or bags, syringes and other medical delivery devices, radiopharmaceutical vials, vial shields, ionization/calibration chamber tubing, waste receptacle, and the like. Additionally, the arrangement of components provided in FIG. 1-3 are examples, and the arrangement of the components may vary among embodiments. Therefore, the wells 24 and troughs 25 may be configured to accommodate these various arrangements and the lengths of tubing necessary to connect the components in such arrangements. Thus, the size, i.e., the width, depth, and length, of the wells 24 and troughs 25 may vary among embodiments. The various recesses and troughs 25 of various embodiments may further include tubing holders for holding tube sections and preventing kinking and tangling.

As used herein, the term "fluid path set" refers to a one or more sections of tubing designed and configured to fluidly connect elements of the fluid delivery system 10 including a medical fluid source, a radiopharmaceutical source, a pharmaceutical source, and the like to a fluid delivery tube configured to deliver medical fluid and the radiopharmaceutical and/or the pharmaceutical to a patient. In various embodiments, the one or more sections of tubing making up the fluid path set 32 may be joined to one another in a manner that allows fluids traveling within the tubing to be carried to various portions of the system 10, mixed with one another, delivered to a patient or a waste receptacle. Thus, the fluid path set 32 may include one or more joints including, but not limited to, linear joints, T-joints, 4-way joints, and the like. In still other embodiments, the one or more of the one or more joints may include valves such as, for example, check valves, bypass valves, stop cocks, and the like, and combinations thereof. The fluid path set 32 of various embodiments may further include one or more linkers that link the fluid path set 32 or portions thereof to the medical fluid, radiopharmaceutical, pharmaceutical, and patient. Such linkers may include luer linkers, screw-type linkers, pressure fittings, and the like.

In some embodiments, tube set may include a delivery tube section 317, that is used on a per-patient basis and discarded after use with a single patient to prevent, for example, cross-contamination between patients that can be collectively be referred to as "single patient delivery systems" ("SPDS") or "patient administration set" ("PAS"). The remaining portions of the fluid path set 32 in which the radiopharmaceutical is calibrated and prepared for delivery can be used for multiple patients and can be referred to as a "multiple patient delivery system" ("MPDS") or "source administration set" ("SAS").

Figure 2B:
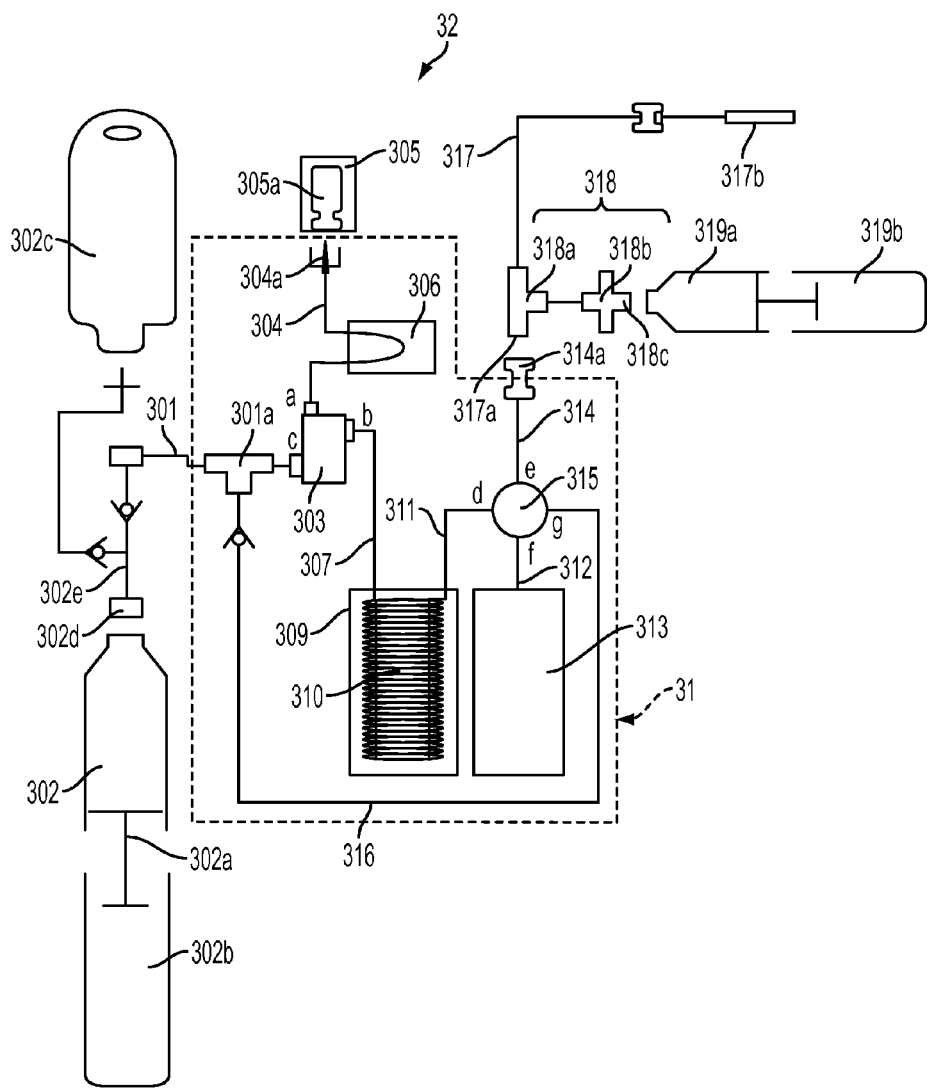
FIG. 2B is a schematic drawing showing the fluid path set and devices contacting the fluid path set of the radiopharmaceutical delivery system of some exemplary embodiments.
Figure 3:
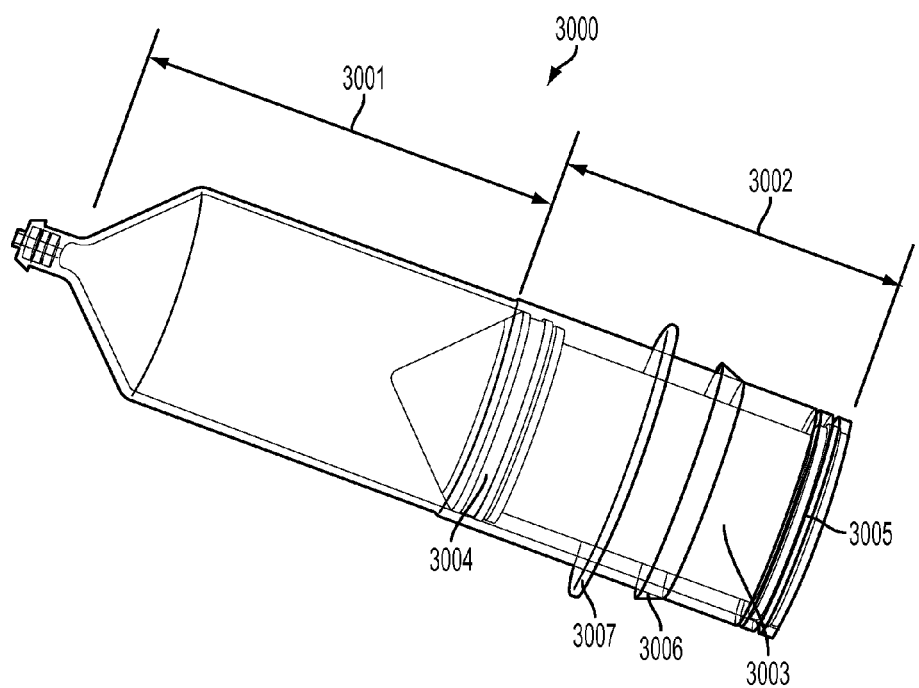
FIG. 3 is a drawing of a dual zone syringe.

FIG. 2B shows schematic of an exemplary fluid path set 32. In such embodiments, a first section of tubing 301 in the fluid path set 32 may be configured to deliver fluid from the medical fluid storage container 302 to a three-way confluence valve 303. In some embodiments, the first tubing section 301 may be configured to be placed within a pump (not shown), and in other embodiments, the medical fluid storage container 302 may be configured to be placed under pressure. For example, in particular embodiments as illustrated in FIG. 2B, the medical fluid storage container 302 may be a rigid, cylindrical device having a stopper or plunger 302a slidably inserted into the fluid storage container thereby creating a seal within the medical fluid storage device. A motor 302b may be operably associated with the stopper or plunger 302a to drive the stopper or plunger 302a into the medical fluid storage device 302 increasing the pressure within the medical fluid storage device 302 and forcing the medical fluid held within the medical fluid storage device 302 in the first tubing section 301. In other embodiments, a peristaltic or inline pump may be associated with the medical fluid storage device to drive fluid from the medical fluid storage device 302 into the first tubing section 301 of the fluid path set 32, and the medical fluid storage device 302 may be prepared from either a rigid or pliable material. The flow of medical fluid and radiopharmaceutical can be regulated throughout the device based on the movement of medical fluid from the medical fluid storage device 302 into the first tubing section 301 either by the stopper 302a and motor 302b or the peristaltic or in line pumping device.

In embodiments including a rigid, cylindrical medical fluid storage device 302, stopper 302a, and motor 302b, the device may further include a means for refilling the medical fluid storage device either manually or automatically. For example, in certain embodiments, a fluid reservoir such as a saline bag 302c, as provided in FIG. 2A, may be removably attached to the medical fluid storage device 302 when the medical fluid storage device 302 has been emptied and can be used to introduce saline, or other medical fluid, into the medical fluid storage device 302. In some embodiments, the first tubing section 301 may be removed during refilling and the fluid reservoir 302c may be attached to the medical fluid storage device 302 through the connector 302d associated with the first tubing section 301. In other embodiments, an auxiliary port 302e may be provided in the medical fluid storage device 302, the connector 302d to the first tubing section 301, or a portion of the first tubing section 301 (shown), and the fluid reservoir 302c may be operably connected to the fluid path through the auxiliary port 302e. In particular embodiments, the fluid reservoir 302c may be detached after the medical fluid storage device 302 has been filled. In other embodiments, the fluid reservoir 302c may remain associated with the medical fluid storage device 302 throughout use of the device and may be used to refill the medical fluid storage device 302 more than one time before being detached from the medical fluid storage device 302.

In certain embodiments, the medical fluid storage device 302 may be a syringe like apparatus, such as the dual zone syringe 3000 of FIG. 3. As illustrated, such a dual zone syringe may have at least two zones, a working zone 3001 which provides a reservoir for the medical fluid and a non-working zone 3002 through which the plunger 3003 passes. The plunger 3003 may include any number of other features and may have any shape. For example, in some embodiments the plunger 3003 may have a cylindrical shape with a conical shaped upper portion, which may facilitate evacuation of the working zone 3001 of the syringe 3000 by substantially matching the shape of the upper portion of the syringe 3000 (as shown). The lower portion of the plunger may be flat or may be shaped to contact a piston or other motor associated with the system 10 that is positioned to advance the plunger 3003 through the syringe 3000 during use. The plunger 3003 may generally include at least two seals, an upper seal 3004 that is in communication with the inner walls of the working 3001 portion of the syringe 3000 and seals fluid within the working zone 3001 and a lower seal 3005 that is in communication with the inner walls of the non-working zone 3002.

The upper and lower seals 3004, 3005 can be effectuated by any means. For example, in certain embodiments, an O-ring may be set within a groove on the portions of the plunger 3003 associated with the upper and lower seals 3004, 3005. In further embodiments, working zone 3001 and the non-working zone 3002 may have different diameters. For example, in some embodiments, the portion of the syringe 3000 making up the working zone 3001 may have a smaller diameter than the portion of the syringe 3000 making up the non-working zone 3002. This arrangement may avoid contamination between the working and non-working zones 3001, 3002. Without wishing to be bound by theory, the inclusion of a sealed non-working zone 3002 may prevent direct contact of ambient air with the inside walls of the working zone 3001 that will contact the medical fluid thereby preserving the sterility of the medical fluid touching the inner walls of the working zone 3001 during repeated use.

The syringe body 3000 may have any external features. For example, as illustrated in FIG. 3, the syringe 3000 may include connector flanges 3006 that circle the diameter of the syringe body 3000 and connect with similar flanges in the body 10 of the system. The syringe body 3000 may further include a stop 3007 that halts advancement of the syringe 3000 into the body 10 during insertion. In certain embodiments, the syringe body 3000 may further include markings that can be read by the system to ensure the proper syringe is being used in the system 10. For example, the system 10 may detect a syringe that is the wrong size or does not include the dual zone system described above, and provide a warning or shut the system down. Such markings may be a visible, radio, or a light tag, and in particular embodiments, the markings may be a series of etched grooves in the syringe body 3000 that can be identified by a light reader in the body of the device. In some embodiments, the markings may be markings as described in U.S. Pat. No. 7,018,363, which is hereby incorporated by reference in its entirety.

A second tubing section 304 may be configured to transport fluid from a first well 305 to the three-way confluence valve 303. In some embodiments, the first well 305 may be configured to accommodate a one or more vial or container of a radiopharmaceutical 305a, and as such, the first well 305 may be individually shielded to reduce radiation exposure to the operator and patient. In other embodiments, the first well 305 may be configured to accommodate a vial or container 305a disposed in a vial shield or pig (as shown). In particular embodiments, the first well 305/205 may further include an individual lid or cap 215 that also may be shielded to reduce radiation exposure (FIG. 2A). The second tubing section 304 may allow transport of the radiopharmaceutical from the first well 305 to the three-way confluence valve 303, and in certain embodiments, the second tubing section 304 may be configured to be placed within a pump 306 which may be a peristaltic or in line pump. In still other embodiments, the second tubing section 304 may include a spike 304a or other device for connecting with the radiopharmaceutical vial 305a and drawing radiopharmaceutical from the vial 305a. In further embodiments, the second tubing section 304 and/or the first tubing section 301 may include additional devices such as, for example, air detection devices, pressure sensors, and the like. Another embodiment (not shown) allows for a second radiopharmaceutical to be connected to the system, creating a system in which two radiopharmaceuticals, e.g., Technesium and Thallium, can be connected to the system 10 simultaneously.

In this configuration, the second radiopharmaceutical would be provided in a second vial in a separate pig. The tubing section associated with radiopharmaceutical would connect include a three way valve connecting tubing section connecting the first radiopharmaceutical to the system 10 and a second tubing section 304 connecting the second radiopharmaceutical to the system 10 before the 306 pump.

The three-way confluence valve 303 may be configured to allow fluid from the first tubing section 301 and/or the second tubing section 304 to individually pass into the third tubing section 307. For example, the three-way confluence valve 303 may be configured to allow fluid to flow from position "c" to position "b" allowing medical fluid from the medical fluid storage device 302 to flow from the first tubing section 301 directly into the third tubing section 307. The three-way confluence valve 303 may be reconfigured based on commands from the control system, described below, to allow fluid to flow from position "a" to position "b" allowing radiopharmaceutical to flow from the second tubing section 304 into the third tubing section 307. In some embodiments, the three-way confluence valve 303 may be configured to allow mixing of medical fluid and radiopharmaceutical by allowing fluid flow through both position "c" and position "a" through position "b" before entering the third tubing section 307.

The third tubing section 307 may lead to a second well 309 that is configured as a ionization/calibration chamber 309. Thus, the second well 309 may include the components necessary to determine the radiation level of the fluid entering the second well 309. For example, in various embodiments, the second well 309 may be associated with the components of detectors such as, but not limited to, a CZT crystal detector, a Geiger-Muller counter, a scintillating counter, or a parabolic detector, such as the parabolic sensor disclosed in U.S. Pat. No. 8,198,599, which is hereby incorporated by reference. The fluid path set 32 may be configured in any way to allow emissions from the radiopharmaceutical to be quantified. For example, in some embodiments, the fluid path set 32 may include a linear loop of tubing contained within the second well 309, and fluid flow may be stopped for a period of time sufficient to allow quantification of the radioactive emissions from the radiopharmaceutical. In other embodiments, as illustrated in FIG. 2B, the second well 309 may be configured to accommodate a coil assembly 310 portion of the fluid path set 32. The coil portion may provide sufficient residence time within the second well 309 to allow for emission from the radiopharmaceutical to be quantified without stopping or slowing fluid flow through the device.

A fourth tubing section 311 may extend from the second well 309 to a three way valve or four way valve 315. As shown in FIG. 2B, a four-way valve 315 may regulate fluid flow from the fourth tubing section 311 through port "d" of the four-way valve into a waste tubing section 312 out port "f" or an output tubing section 314 out port "e." The four-way valve may further regulate fluid flow from an auxiliary tubing section 316 through port "g" that is separately associated with the medical fluid source 302 into the waste tubing section 312 out port "f" or output tubing section 314 out port "e." In such embodiments, the output tubing section 314 may extend away from the four-way valve toward a delivery tubing section 317 through which the radiopharmaceutical is delivered to the patient. The waste tubing section 312 may extend away from the four-way valve to carry fluid to a waste receptacle 313 and function to divert from, for example, a priming procedure to prepare the system 10 for injection away from delivery tubing section 317 and ultimately the patient. The auxiliary tubing section 316 may be associated with a T-joint or three-way valve 301a and may extend from the first tubing section 301 to the four-way valve 315. The auxiliary tubing section 316 may be configured to transport fluid from the medical fluid source 302 directly to the four-way valve 315 providing a by-pass for the majority of the fluid path while allowing flow of medical fluid to the fluid delivery section 317 and patient.

The four-way valve of some embodiments may be designed as illustrated in FIG. 2C I. FIG. 2C shows a four-way valve 2100 having a rotating internal stem 2101 and an external four-way tubing connectors 2102. In some embodiments, the four-way tubing connector 2102 may be prepared from a flexible material that has sufficient tensile strength to allow the valve to maintain a seal between the internal stem 2101 and the tubing connector 2102, and in other embodiments and rigid external tubing connector 2012 may be coupled to an semi-rigid or rotating internal stem. In other embodiments, the internal stem 2102 may include distal separations 2103 that allow the stem 2102 to be compressed slightly allowing for the tubing connector 2102 to be placed over internal stem 2101 during manufacture. In the cross-sectional view provided in FIG. 2C II, the passageway 2106 through the internal stem 2101 can be seen. The passageway 2106 may be configured to allow passage of fluid through the passageways, 2102a and 2102b in this drawing, of neighboring tubing extensions only while sealing off the remaining passageways 2102c and 2102d. In various embodiments, the stem may be designed to press-fit into to the body 11 of the device when the MPDS is properly positioned on the device.

The auxiliary or by-pass tubing section 316 may allow for the delivery of different fluids to a patient without mixing. For example, in some embodiments, medical fluid may be passed directly from the medical fluid storage container 302 through the auxiliary or by-pass tubing section 316 to the four-way valve 315 which directs the medical fluid to the output tubing section 314 and the delivery tubing section without mixing with radiopharmaceutical or other fluids contained within the remainder of the fluid path set 32. Thus, the patient may continually receive medical fluid even when radiopharmaceutical is not being delivered. This arrangement further allows for the delivery of pharmaceutical from the pharmaceutical delivery port 318 (described below) without the administering radiopharmaceutical.

In still further embodiments, the system may include additional auxiliary tubing sections (not shown). Such additional auxiliary tubing sections may carry any medical fluid to the patient and additional auxiliary tubing sections may integrate into the tubing set through 5-, 6-, 7-, or 8-way valves positioned in place of the four-way valve 315 described above, or additional 3-, 4-, 5-, or 6-way valves may be incorporated into the tube set at one or more locations, such as, for example, in the output tubing section 314. In various embodiments, additional auxiliary tubing sections may be associated with saline or other medical fluids, pharmaceutical, or other fluid that may be required for particular patients. The multiport valves of various embodiments including the four-way valve 315 described above may be commercially available multi-port valves or may be specially designed to limit mixing between input tubes.

In yet further embodiments including a three way valve (not shown), the auxiliary tubing section 316 may be absent. The fourth tubing section 311 may deliver fluid to the three way valve where the fluid can be diverted from port "d" through port "f" into the waste tubing section 314 and waste receptacle or bag 313 or from port "d" through port "e" to the output tubing section 314 and toward the delivery tubing section 317.

In some embodiments, the sixth tubing section may terminate in an output fitting 314a, which may be a connector or adaptor, or other fitting configured to operably connect the output tubing section 314 to the delivery tubing section 317. In particular embodiments, the connector at the terminus of the output tubing section 314 may be a swabable valve that can be disinfected or washed when the delivery tubing section 317 is replaced between patients.

The MPDS 31 portion of this fluid path set 32 may include any tubing section from the medical fluid storage device 302 to the connector 314a of the output tubing section 314 and is indicated by the components within the dashed line box. In various embodiments, the MPDS 31 may include a connector 302d such as a spike or luer lock for connecting the MPDS 31 to the medical fluid storage device 302; a spike or vented cannula 304a for connecting to radiopharmaceutical vial; a coil assembly 310; a connector for a waste receptacle (not shown); a connector for the output tubing section 314; and various connectors and tube sections connecting these elements. In some embodiments, the MPDS may further include the various valves as described above, 303, 301a, 315. In certain embodiments, the connector 302d for connecting the MPDS 31 to the medical fluid storage device 302 may include a means for sensing the MPDS 31 and the medical fluid storage device 302. Embodiments are not limited to a particular sensing device. For example, a tag including a bar code or radiofrequency identification (RFID) may be associated with MPDS 31 may be read by the connector 302d or at the connection site to ensure that the proper MPDS 31 is connected to the system. In other embodiments, an optical system such as that described in U.S. Pat. No. 7,018,363 may be used to encode the connectors.

Figure 2D:
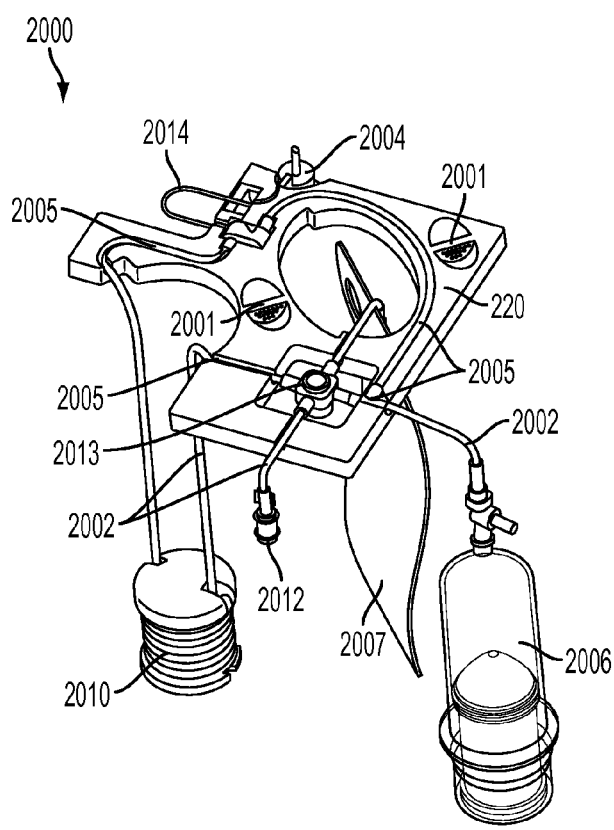
FIG. 2D is a drawing showing an exemplary multiple patient disposable set (MPDS) in a holder.

Each component of the MPDS 31 may be pre-connected and can be stored in a sterile packet or container for use in a fluid delivery system, and in certain embodiments, the upper portion of the body may be configured to accept a tray or holder 220 designed to hold and separate the components of the MPDS 31 in a position to be inserted into the troughs 25 and wells 24 of the device without realignment by the operator. FIG. 2D shows the contents of a sterile packet 2000 which includes the holder 220, which can have one or more grips 2001 configured to be grasped by the user during insertion and removal of the MPDS 31 from the system 10, and various troughs 2005 for routing the tubing sections 2002. The packet 2000 may further include a medical fluid storage reservoir or a container, such as the syringe 2006 provided in FIG. 2D, for storing and introducing medical fluid such as saline into the fluid path set 32, a waste receptacle 2007, and a coil assemble 2010 that can be incorporated into an ionization chamber. A spike or vented cannula 2004 for connecting the tube set to a vial of radiopharmaceutical and a fitting such as a luer connector 2012 for connecting the MPDS to an SPDS. The packet also includes the various tubing sections necessary to connect these elements as well as valves or tubing configured to be incorporated into a valve 2013, and sections of tubing configured to be introduced into pumps 2014. Using the holder 220 and the packet 2000, the operator can introduce the MPDS 31 into the system without individually inserting each tube section, valve or connector into the system. Rather, the user can introduce the tube set into the system by merely placing the holder 220 into the corresponding groove in the device 10, inserting the medical fluid storage reservoir or a container 2006, waste receptacle 2007, and coil assemble 2010 into the appropriate wells, and connecting the tube set to the pumps where appropriate.

The container or vial of radiopharmaceutical may be any suitable container known in the art and the well 24 for holding the radiopharmaceutical may be configured to accept any such container or vial and securely hold the container during use. In some embodiments, an adaptor may be used that encases all or a portion of the vial or container before it is placed in the well 24 to ensure that the vial or container is secured within the well 24. In still further embodiments, the adaptor may be prepared from or include a material that blocks emission of the radioactive particles from the radiopharmaceutical.

In particular embodiments, the vial or container may be a multi-dose container configuration to hold and store a sufficient amount of radiopharmaceutical for delivery to a plurality of patients in a single container. In other embodiments, the well 24 may be configured to hold more than one container or vial for holding and storing radiopharmaceuticals. In some embodiments, each container in the multi-container configuration may include individual doses of radiopharmaceutical sufficient for administration to a single patient. In other embodiments, each container or vial may hold and store multiple doses of the radiopharmaceutical and the system may be configured such that doses of the radiopharmaceutical can be pulled from a new vial when the proceeding vial is used to completion. In still other embodiments, a different radiopharmaceutical composition may be held and stored in each of two or more different multi-dose containers, and in such embodiments, the system may be configured to deliver different radiopharmaceutical compositions either simultaneously to a single patient or consecutively to different patients during different procedures. In still further embodiments, a micro-fluidic device or other radiopharmaceutical generation technology capable of real-time generation of a radiopharmaceutical can be included as part of the multi-dose container configuration.

The system may further include a pharmaceutical delivery port that includes a a 3-way connector 318a, a check valve 318b that only allows fluid to flow one-way from the stress agent to the main line only, and a connector 318c for connecting a syringe or vial including a pharmaceutical agent such as a stimulant to the system thereby providing a pharmaceutical delivery port 318. In some embodiments, the pharmaceutical delivery port 318 makes up a portion of the delivery tubing section 317 (as illustrated in FIG. 2B). In other embodiments, the pharmaceutical delivery port 318 may be incorporated into the output tubing section 314 between the three or four-way valve 315 and the connector 314a. The pharmaceutical delivery port may be any type of port known in the art such as, but not limited to, a luer, a needle vial adaptor, needleless vial adaptor, or other fitting capable of accepting a delivery device 319a such as a syringe or vial. The delivery port may further include a T-joint or a three way valve or stopcock. The pharmaceutical delivery port 318 may be configured to allow for the introduction of a pharmaceutical agent into the delivery tubing section 317 during a procedure. For example, in some embodiments, a syringe 318a holding a pharmaceutical agent may be fitted to the pharmaceutical delivery port 318, and the pharmaceutical agent may be introduced into the delivery tubing section 317 during the procedure either manually by depressing a plunger in the syringe 319a or automatically using a motor associated with the plunger or a pump 319b delivering an appropriate dose of the pharmaceutical to the patient. In other embodiments, fluid may be diverted into the syringe or vial by the pharmaceutical delivery port 318 where the pharmaceutical is mixed with the fluid before being introduced back into the pharmaceutical delivery port 318 and out to the delivery tube section 317. In additional embodiments, the system may include one or more pumps, motors, or the like associated with the pharmaceutical delivery port 318, delivery device 319, output tubing section 314, or delivery tube section 317. In some embodiments, the SPDS connector 317a can be encoded through RFID, light sensors, mechanical sensors, etc. to ensure that the correct SPDS is connected. This ensures that the correct protocol is executed with the correct SPDS.

The sixth tube section 314 and the delivery tube section 317 may be an integral part of the fluid path set 32, or in other embodiments, the delivery tube section 317 and/or the sixth tube section 314, pharmaceutical delivery port 318, and other components associated with this portion of the fluid path set 32 may be one or more separate fluid path sets configured to attach to the fluid path set 32 by, for example, a luer fitting or swabable valve. For example, in some embodiments as illustrated in FIG. 2B, the delivery tube section 317 may include a first end 317a that can be reversibly attached to the connector 314a associated with the output tubing section 314 and a patient end 317b having a connector such as a luer connector, that is capable of being attached to, for example, a catheter, IV needle, intravenous port, or the like that can be used to deliver the radiopharmaceutical to a patient. In other embodiments, the delivery tube section 317 may have a first end that can be reversibly attached to the pharmaceutical delivery port 318 or a T-joint or three-way valve associated with the fluid delivery port 318c. In still other embodiments, the delivery tubing section 317, the output tubing section 314, and any intervening device or tube section such as the pharmaceutical delivery port may be separately, reversibly connected to the fluid path set 32. In some embodiments, the pharmaceutical delivery port may be absent, blocked, or otherwise eliminated such that the radiopharmaceutical can be delivered in the absence of the addition of an additional pharmaceutical or stimulating agent.

Embodiments are not limited to a particular pharmaceutical agent, and any agent that is known or may be usefully administered may be contained within the syringe 319a and administered to the patient during a procedure. For example, in some embodiments, the pharmaceutical agent may be a stress agent such as, but not limited to, IV Dobutamine, IV Dipyridiamole (Persantine), IV Adenosine (Adenoscan), IV Lexiscan (Regadenoson), and the like. In other embodiments, the pharmaceutical agent may reduce vasodilation such as, for example, IV Aminophylline. In still other embodiments, the system may include a first pharmaceutical delivery port 318 and a second pharmaceutical delivery port (not shown). In such embodiments, a first syringe associated with the first pharmaceutical delivery port that holds a stress agent and a second syringe associated with the second pharmaceutical deliver port may include a pharmaceutical that acts to reduce vasodilation and act as an antidote to stress agent, allowing the user to reduce the stress under which the patient is placed as part of the procedure or as a precaution in the event of an adverse event. The pharmaceutical agent can be introduced into the fluid flow through the pharmaceutical delivery port continuously or in one or more controlled doses.

The delivery tube section 317 may be configured to connect to typical patient delivery apparatuses such as, IV needles, ports, catheters, or other means for delivering intravenous pharmaceuticals. In other embodiments, the delivery tube section 317 may incorporate such delivery devices. In still other embodiments, the delivery tube section 317 may be configured to connect to other sections of tubing, which may incorporate the delivery apparatuses.

In some embodiments, the system 10 may include one or more additional components including, but are not limited to, pinch valves, air detectors, and mounts or retainers for holding the connector ends of the delivery tube section, and the like and combinations thereof. In particular embodiments, pinch valves may be powered and controlled by the fluid delivery system 10, and/or manually operated. In other embodiments, the pinch valves can be replaced with a manual or automated 3-way stop cock. The fluid delivery system 10 may include one or more pumping mechanisms configured to facilitate the movement of liquids from wells in the body to the delivery tube section 317 of the fluid path set 32 at any position in the system 10. Any suitable type of pumping mechanism can be used including, but not limited to, piston-driven syringe pumps, gear pumps, rotary pumps, in-line pumps, and peristaltic pumps. In some embodiments, the pumping mechanism may be peristaltic pump. In various embodiments, the pumping mechanism may be opened to receive a length of tubing associated with the fluid path set 32.

The output tubing section 314 may terminate in a connector 314a configured to connect the MPDS 31 with an SPDS 32. In some embodiments, the connector end 314a of the MPDS 31 may be a swabable luer valve that is biased to close or seal off the connector end 314a of the MPDS 31 when the SPDS 32 is not connected. The swabable luer valve prevents the MPDS 31 from being contaminated and allows an operator to swab or clean the connector end 314a using, for example, an alcohol wipe, prior to connecting an SPDS 32 to the connector. In other embodiments, the connector end 314a may be a standard luer connector or another connector as known in the art.

The tubing of each of the sections of the MPDS 31 and SPDS 32 may be prepared from the same or different materials. For example, in various embodiments, the tubing may be silicone, C-Flex, standard PVC, silicone-like PVC material, or pump tubing. In particular embodiments, the microbore tubing of second tubing section 304 may be formed from, for example, silicone, C-Flex, or silicone-like PVC material, and the other tubing sections 301, 307, 311, 312, 314, 317, and tube coil 310 may be formed from any suitable polymeric material, including standard PVC.

The dimensions of the components of the MPDS 31 as shown in FIG. 3, including the various tubing sections, may vary among embodiments and may depend, for example, on the procedure for which the system is being used and the type and amount of radiopharmaceutical being delivered. In certain exemplary embodiments, the first tubing section 301 may be about 3 inches to about 4 inches in length or 3.4 inches in length, may have an outer diameter (OD) of about 0.05 inches to about 0.25 inches or about 0.17 inches and an inner diameter (ID) of about 0.05 inches to about 0.15 inches or about 0.08 inches, and may have an about 90 to about 95 Shore A durometer. The second tubing section 304 may be about 7 inches to about 10 inches in length or about 8.9 inches in length and can be formed of microbore tubing having an OD of about 0.05 inches to about 0.10 inches or about 0.09 inches, an ID of about 0.01 inches to about 0.07 inches or about 0.03 inches and an about 35 to about 55 or about 45 Shore A durometer. The use of microbore tubing in second tubing section 304 improves volume accuracy and thereby improves measured activity accuracy (i.e., of pharmaceutical delivered to the patient) and reduces radiopharmaceutical waste. The third tubing section 307 may be about 9.0 to about 14 inches in length or about 11.75 inches in length, may have an OD of about 0.05 inches to about 0.25 inches or about 0.17 inches and an ID of about 0.05 inches to about 0.15 inches or about 0.08 inches, and may have an about 90 to about 95 Shore A durometer. The fourth tubing section 311 may be about 8.0 inches to about 12 inches in length or approximately 10.5 inches in length, may have an OD of about 0.05 inches to about 0.25 inches or about 0.17 inches and an ID of about 0.05 inches to about 0.15 inches or about 0.08 inches, and may have an about 90 to about 95 Shore A durometer. The waste tubing section 314 and the output tubing section 314 may each be about 1.0 inches to about 5.0 inches in length or approximately 3.0 inches in length, may have an OD of about 0.05 inches to about 0.25 inches or about 0.17 inches and an ID of about 0.05 inches to about 0.15 inches or about 0.08 inches, and may have an about 90 to about 95 Shore A durometer. The tubing in tube coil 310 may be from about 20 inches to about 55 inches in length or approximately 41.75 inches in length, has an OD of about 0.10 inches to about 0.30 inches or about 0.22 inches and an ID of about 0.05 inches to about 0.20 inches about 0.16 inches, and may have an about 90 to about 95 Shore A durometer. All of these dimensions are provided for exemplary purposes only and are not to be construed as limiting the present disclosure.

The MPDS 31 may include a coil assembly 310. The coil assembly 310 may, generally, include a section of that is simply gathered tubing in a coiled or an uncoiled, amorphous fashion and placed inside ionization/calibration chamber 309. In some embodiments, the coil assembly may be an individually constructed unit, and in other embodiments, the coil assembly 310 may include all or portions of third tubing section 307 and fourth tubing section 311. The coil assembly 310 of various embodiments positions the radiopharmaceutical such that the radioactivity level of the radiopharmaceutical in the tube coil 310 can be measured by the components surrounding the ionization/calibration chamber 309. More specifically, the coil assembly 310 orients and locates the radiopharmaceutical within a "linear region" of the ionization/calibration chamber 309 to more accurately measure its activity level and prepare an optimal dose for injection into a patient.

Figure 4A:
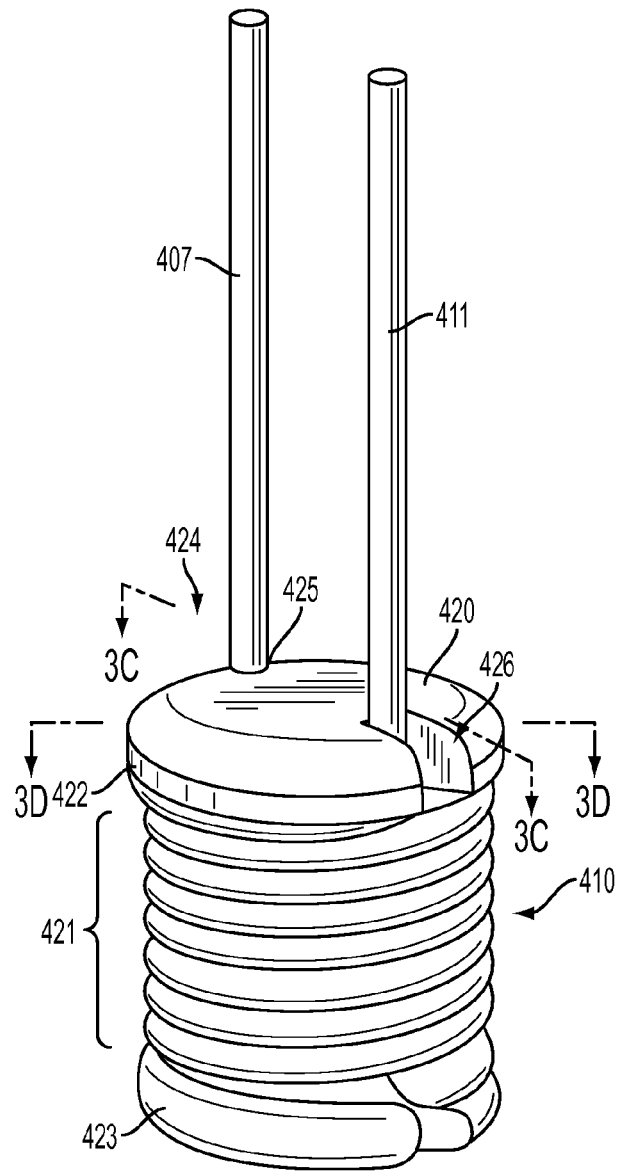
FIG. 4A is a schematic drawing showing external features of the tube coil of the radiopharmaceutical delivery system of some exemplary embodiments.

In some embodiments, the tubing may be coiled on itself or stacked in a coil by bonding the tubing layers, and in other embodiments, as illustrated in FIG. 4A, the coil assembly 410 may include a core element or structure 420 that is configured to allow the tube coil 410 to be wrapped around the core element 420. As such, the tube coil 410 can be formed on the core element 420. The core element 420 may be configured to facilitate optimal positioning of the tube coil 410, and may be sized to fit within the ionization/calibration chamber 309 of the body 11. In some embodiments, the core element 420 may include a tube channel 421 between an upper shoulder 422 and a lower shoulder 423. The tube coil 410 may be retained within the tube channel 421 and between the upper and lower shoulders 422, 423 to hold the tube coil 410 in position and prevent kinking. In further embodiments, an upper surface 424 of core element 420 may include one or more inlet channels or grooves 425 and an outlet channel or groove 426 to accommodate third tubing section 407 and fourth tubing section 411, respectively.

In various embodiments, the coil assembly 410 may be positioned concentrically in the ionization/calibration chamber 309. In some embodiments, the core element 420 may be self-centering when inserted into the ionization chamber 309 of the fluid delivery system 10 to facilitate optimal positioning and performance. This may be achieved either through structural features of the coil assembly 410, the structure of core element 420, or a combination thereof. For example, in some embodiments, the upper shoulder 422, the lower shoulder 423, or both can be configured to associate with an outer wall of the ionization/calibration chamber 309. For example, the core element 420 may include additional features such as, for example, extensions, indentations, or notches may be provided on the core element 420 either on the upper or lower shoulders 422, 423 or another portion of the coil assembly 410, that engage corresponding elements in the ionization/calibration chamber 309 to aid in the proper positioning of the tube coil 410. In other embodiments, the lower shoulder 423 may be sized to provide an appropriate distance between the lower surface of the ionization/calibration chamber when the lower shoulder contacts the lower surface of the ionization/calibration chamber or a diameter that corresponds with a the appropriate diameter of the ionization/calibration chamber 309.

Figure 4B:
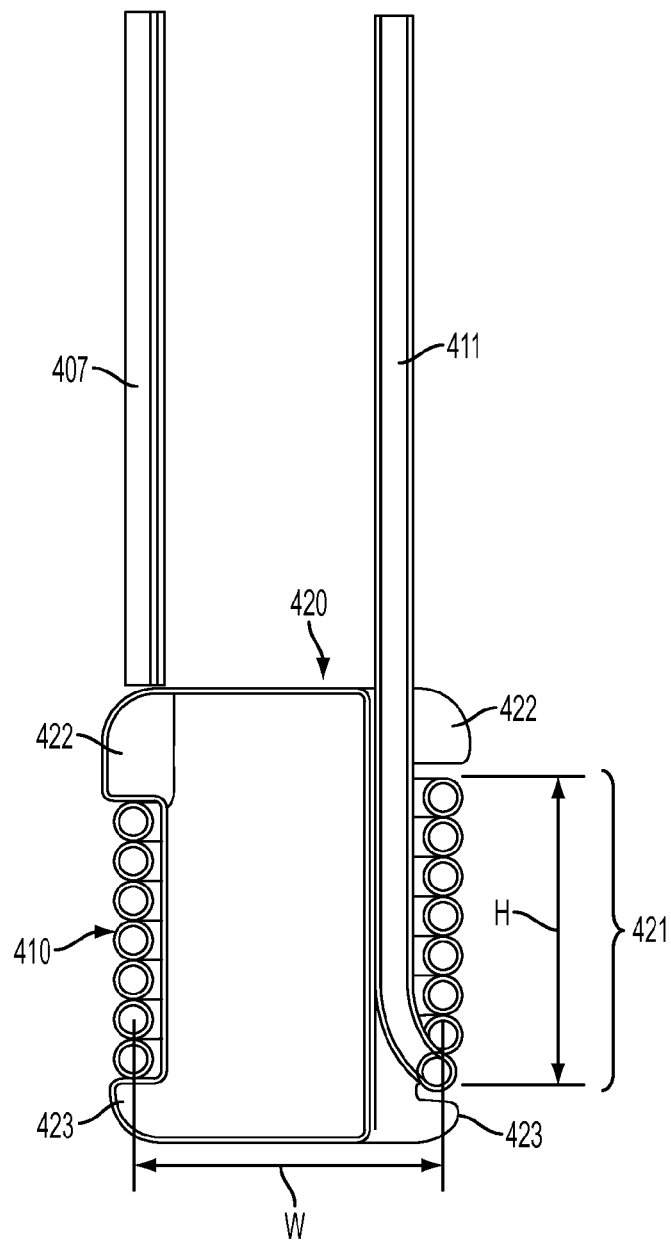
FIG. 4B is a schematic drawing showing a cross-section of the tube coil of the radiopharmaceutical delivery system of some exemplary embodiments.

With reference to FIG. 4B, in particular embodiments, the core element 420 and the tube coil 410 may be sized and dimensioned so that the coil assembly 410 can be optimally positioned within the "linear region" of the ionization/calibration chamber 309. The "linear region" of an ionization chamber refers to the region of the chamber in which activity level measurements are repeatable and predictable. For an exemplary ionization/calibration chamber (Model IK-102 Short Ionization Chamber provided by Veenstra Instruments), the "linear region" is located within a window of about 5 mm to about 65 mm measured from the base or bottom wall of the ionization/calibration chamber 309. The tube coil 410 of various embodiments may have a volume capacity of about 1 ml to about 10 ml or about 1.5 ml to about 7 ml and may be configured in any way to achieve the desired volume. Moreover, the tube coil 410 may have any number of turns. For example, in some embodiments, the tube coil 410 may have about 4 to about 10 turns, and in other embodiments, the tube coil 410 may have about 5 to about 7 turns. In various embodiment, the tube coil may have one or more ½ or ¼ turns that allow appropriate placement of the third tube section 407 and fourth tube section 411. A tube coil having this number of turns may be formed from an length of tubing sufficient to make the desired number of turns based on the diameter of the core element 420. For example, a core element having a diameter (w) of about 0.5 in to about 4 in or about 1 in to about 3 may require tubing having a length of about 5 in to about 24 in, about 8 in to about 15 in, or about 10 in to about 12 in. The height (h) of the tube coil 410 may similarly vary depending on the number of turns, the diameter of the tubing, and the diameter to the core element. For example, a tube coil 410 having from about 5 to about 7 turns may have a height (h) of from about 0.5 in to about 8 in or about 1 in to about 5 in. The tube coil 410 may be prepared from any type of tubing; however, in certain embodiment, the tubing may have an OD of from about 0.01 in to about 0.5 in and an ID of about 0.025 to about 0.5 in.

Figure 5:
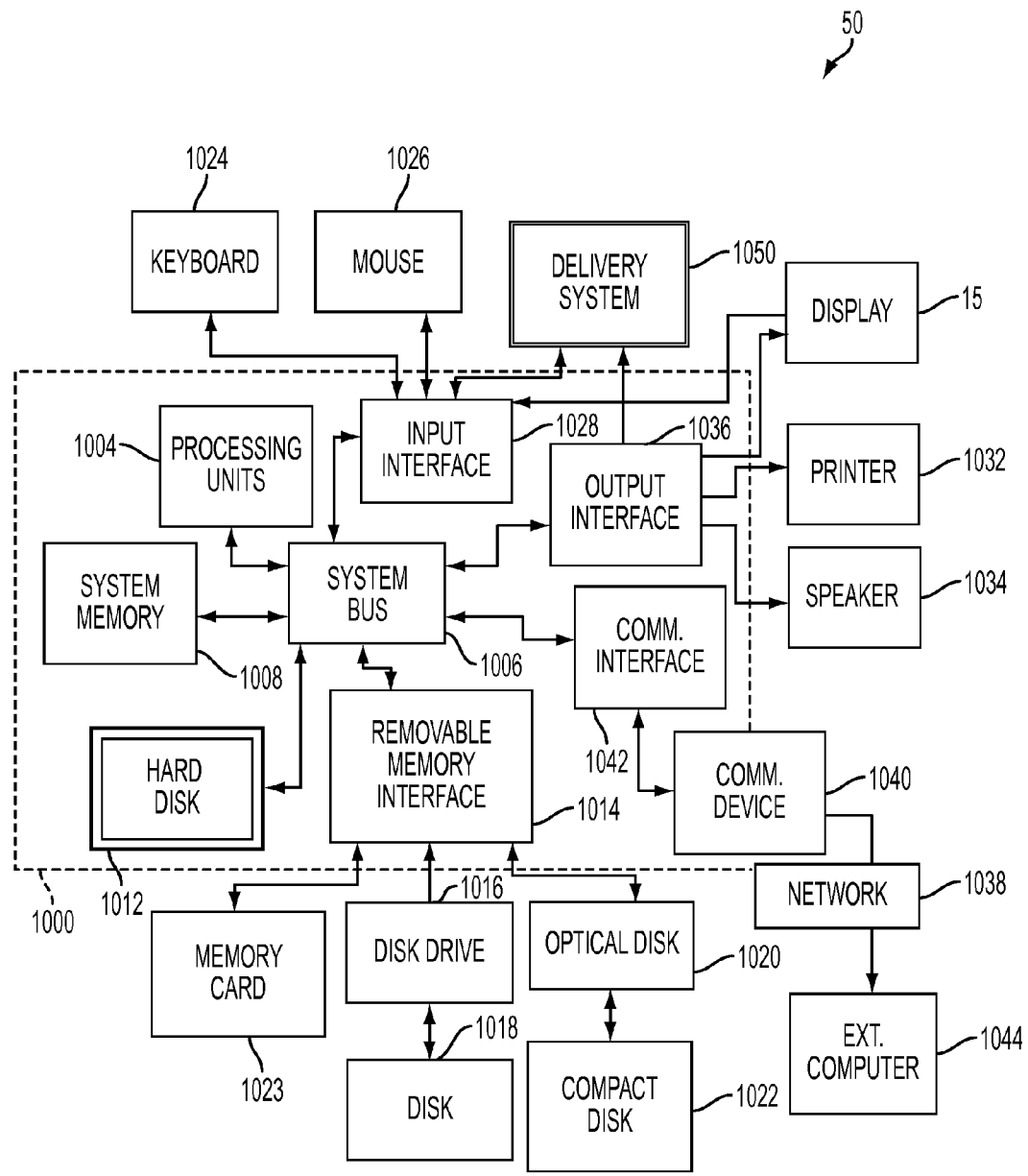
FIG. 5 is a schematic representing the control system of the radiopharmaceutical delivery system of some exemplary embodiments.

In various embodiments, the fluid delivery system 10 may include a control system 50 (schematically represented in FIG. 5) in communication with the various components of the injector system 1050 that for the purposes of the schematic of FIG. 5 can, include, for example, pumps, motors, ionization/calibration chamber, interrupt button, air detectors valves, stopcocks, and the like. The control system 50 may, generally, control the operation of the injector system 1050, while also providing an interface with input and output devices such as the display 15, printer 1032, and network devices 1040 used to program and direct the action of the injector system 1050.

The control system 50 may include, but is not limited to, at least one computer 1000 having certain components for appropriate operation, execution of code, and creation and communication of data. The computer 1000 includes one or more processing units 1004 (typically referred to as a central processing unit or CPU) that serves to execute computer-based instructions received in the appropriate data form and format. Further, this processing unit 1004 may be in the form of multiple processors executing code in series, in parallel, or in any other manner for appropriate implementation of the computer-based instructions. As used herein, the computer 1000 may be operably configured to execute appropriate software to perform and implement the processing steps of the methods and systems disclosed herein. The system may include one or more computers 1000 or similar computing devices having a computer-readable storage medium capable of storing computer-readable program code or instructions that cause the processing unit 1004 to execute, configure, or otherwise implement the methods, processes, and transformational data manipulations discussed herein. Still further, the computer 1000 may be in the form of a personal computer coupled to the fluid delivery system 10, a processor formed integrally with the fluid delivery system 10, a computer provided remotely from the fluid delivery system 10, or any other type of computing device having the necessary processing hardware to appropriately process data to effectively implement the method and system described herein.

The control system 50 may further include a system bus 1006 to facilitate appropriate data communication and processing information between the various components of the computer 1000. The system bus 1006 may be any of several types of bus structures, including a memory bus or memory controller, a peripheral bus, or a local bus using any of a variety of bus architectures. In particular embodiments, the system bus 1006 may facilitate data and information communication between the various components (whether internal or external to the computer 1000) through interfaces.

In some embodiments, the computer 1000 may include one or more discrete computer-readable media components. For example, computer-readable media may include any media that can be accessed by the computer 1000, such as volatile media, non-volatile media, removable media, non-removable media, and the like. In certain embodiments, the computer-readable media may include computer storage media, such as media implemented in any method or technology for storage of information such as computer-readable instructions, data structures, program modules, or other data, including, but not limited to, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 1000. In some embodiments, the computer-readable media may include communications media, such as computer-readable instructions, data structures, program modules, or other data in a modulated data signal such as a carrier wave or other transport mechanism. In other embodiments, the computer-readable media may include any information delivery media, wired media (such as a wired network and a direct-wired connection), and wireless media (such as acoustic signals, radio frequency signals, optical signals, infrared signals, biometric signals, bar code signals, etc.). Combinations of any of the above are also included within the scope of computer-readable media.

In still other embodiments, the computer 1000 may further include system memory 1008 with computer storage media such as volatile and non-volatile memory, ROM, and/or RAM. A basic input/output system (BIOS) with appropriate computer-based routines assists in transferring information between components within the computer 1000 and can be stored in ROM. The RAM portion of the system memory 1008 typically contains data and program modules that are immediately accessible to or presently being operated on by processing unit 1004, e.g., an operating system, application programming interfaces, application programs, program modules, program data, and other instruction-based computer-readable code.

The computer 1000 may also include other removable or non-removable, volatile or non-volatile computer storage media products. For example, the computer 1000 may include a non-removable memory interface 1010 that communicates with and controls a hard disk drive 1012, i.e., a non-removable, non-volatile magnetic medium, a removable, non-volatile memory interface 1014 that communicates with and controls a magnetic disk drive unit 1016 (which reads from and writes to a removable, non-volatile magnetic disk 1018), an optical disk drive unit 1020 (which reads from and writes to a removable, non-volatile optical disk, such as a CD ROM 1022), a Universal Serial Bus (USB) port for use in connection with, for example, a removable memory card 1023. Other removable or non-removable, volatile or non-volatile computer storage media can be used in the exemplary computing system environment 1002, including, but not limited to, magnetic tape cassettes, DVDs, digital video tape, solid state RAM, solid state ROM, and the like. These removable or non-removable, volatile or non-volatile magnetic media are in communication with the processing unit 1004 and other components of the computer 1000 via the system bus 1006. The drives and their associated computer storage media discussed above and illustrated in FIG. 4A provide storage of operating systems, computer-readable instructions, application programs, data structures, program modules, program data, and other instruction-based computer-readable code for the computer 1000 (whether duplicative or not of the information and data in the system memory 1008).

In particular embodiments, the fluid delivery system 10 may be configured to allow a user to enter commands, information, and data into the computer 1000 using the touchscreen of the GUI display 15 via an operator input interface 1028. However, it has been envisioned that an operator may enter commands, information, and data into the computer 1000 using other attachable or operable input devices, such as a keyboard 1024, a mouse 1026, a remote control device, a microphone, a trackball, a joystick, a touchpad, a scanner, a tablet computer, and the like, via the operator input interface 1028. Any arrangement that facilitates the input of data and information to the computer 1000 from an outside source may be used including, for example, hard wiring or accessing using a wireless network device, such as Bluetooth, a wireless internet connection, or a cellular connection. As discussed, these and other input devices are often connected to the processing unit 1004 through the operator input interface 1028 coupled to the system bus 1006, but may be connected by other interface and bus structures, such as a parallel port, game port, or a USB.

In still further embodiments, data and information can be presented or provided to an operator in an intelligible form or format through certain output devices, such as the GUI display 15 (to visually display this information and data in electronic form), a printer 1032 (to physically display this information and data in print form), a speaker 1034 (to audibly present this information and data in audible form), etc. All of these devices are in communication with the computer 1000 through an output interface 1036 coupled to the system bus 1006.

The computer 1000 may operate in a network environment 1038 through the use of a communications device 1040, which is integral to the computer or remote. This communications device 1040 is operable by and in communication with the other components of the computer 1000 through a communications interface 1042. Using such an arrangement, the computer 1000 may connect with or otherwise communicate with one or more remote computers, such as a remote computer 1044 of a hospital information system, which typically includes many or all of the components described above in connection with the computer 1000. Using appropriate communications devices 1040 such as, for example, a modem, a network interface, adapter, telephone line, cellular telephone connection, wifi network, and the like, the computer 1000 may operate within and communicate through a local area network (LAN) and a wide area network (WAN), but may also include other networks such as a virtual private network (VPN), an office network, an enterprise network, an intranet, the Internet, and the like and combinations thereof. It will be appreciated that the network connections shown are exemplary and other means of establishing a communications link between the computers 1000, 1044 may be used.

Generally, the fluid delivery system of embodiments described above may be configured to deliver a radiopharmaceutical drawn from a bulk radiopharmaceutical vial 305a in FIG. 2B. A dose of the radiopharmaceutical may be withdrawn from the bulk radiopharmaceutical vial 305a contained in the first well 305, and passed though the coil assembly 310 of the fluid path set 32 in the ionization/calibration chamber 309. The radioactive activity, i.e., the average emission of the dose of radiopharmaceutical, can be determined based on measurements made in the ionization/calibration chamber 309. The system may be configured to determine the volume of a dose having a desired activity level based on the measured amount of radioactive activity and the volume of a test sample. The system may then draw the proper amount of radiopharmaceutical to deliver the appropriate dose of radiopharmaceutical as identified by the user to the patient.

The fluid delivery system 10 may further be configured for priming (i.e., purging air from the MPDS 31), delivering a radiopharmaceutical to a patient, providing a saline flush to remove residual radiopharmaceutical, while minimizing or eliminating exposing the individuals operating system to the radiopharmaceutical and minimizing or eliminating contaminated waste. Moreover, MPDS 31 and other elements disclosed herein also facilitate safe delivery of the pharmaceutical to multiple destinations (for example, dose delivery to a series of patients).

The system 10 may be further configured to provide feedback information to the operator. For example, in some embodiments, the system may provide the operator with information regarding the administration such as, but not limited to, the dosage of radiopharmaceutical delivered to the patient by milligram (mg), volume (ml), and/or radioactive activity (mCi), the amount of other pharmaceutical composition delivered to the patient (mg/ml), the flow rate of the radiopharmaceutical or other pharmaceutical (ml/s), the amount of saline administered (ml), dosing time (i.e., the time required for delivery), the delivery time (i.e., the time of day), date, and the fluid pressure in the delivery system during delivery. In particular embodiments, the system may further provide the operator with absorption data with regard to the particular radiopharmaceutical administered including the expected amount of the radiopharmaceutical absorbed by particular organs such as brain, lung, liver, kidney, bladder, bone, thyroid, heart, breast, stomach, colon, and skin. In some embodiments, the system may reference patient data to determine the amount of radiopharmaceutical administered to the particular patient over time and provide a warning to the operator if absorbed levels become too high. In various embodiments, the information may be provided to the operator in real time or provide an estimate of the absorption, based on the planned dose, prior to an injection.

Following administration or the completion of an administration protocol, the system may provide a summary of the procedure including any relevant data. For example, in various embodiments, the system may provide the dosage of radiopharmaceutical delivered to the patient by milligram (mg), volume (ml), and/or radioactive activity (mCi), the amount of other pharmaceutical composition delivered to the patient (mg/ml), the flow rate of the radiopharmaceutical or other pharmaceutical (ml/s), the amount of saline administered (ml), dosing time (i.e., the time required for delivery), the delivery time (i.e., the time of day), date, and the fluid pressure in the delivery system during delivery and the like and combinations thereof. The system may further provide absorption data such as that described above.

The data provided either in real time during performance of the protocol or in summary of the procedure may be provided numerically or graphically, and in certain embodiments, the screens providing the data may provide both numeric and graphic data simultaneously.

The system may further provide the patients name and any critical data such as, height, weight, allergies, disease being treated or tested for, the procedure to be performed, the location of the injection/infusion site, and the like and various combinations thereof. Such data may be inputted at the time of the procedure or may be inputted prior to the procedure. In certain embodiments, the operator may input the patients name and the system may retrieve appropriate patient data from electronically archived patient records using a computer network or Internet connection. In still further embodiments, the system may store patient information for more than one procedure. For example, in some embodiments, a patient schedule including a series of patient scheduled to undergo procedures in the course of a number of hours, a day, a week, and so on or any time period therebetween, may be inputted into the system and the system may store patient information for the time period necessary to complete the procedures scheduled. As above, patient data for the schedule may be provided in advance of completion of the patient schedule, or the system may retrieve patient information from electronic patient archives.

The system may further be configured to run a self-check to determine, for example, the level of various fluids in the system, including the amount of radiopharmaceutical remaining, the amount of medical fluid remaining, the amount of the other pharmaceutical remaining, the amount of waste, and the like and combinations thereof. In some embodiments, the system may be configured to provide a warning when insufficient radiopharmaceutical, other pharmaceutical, or medical fluid remains to complete a procedure, or the waste receptacle reaches a particular level of fullness. The system may further provide information regarding the internal pressure, temperature of the system or portions thereof, computer system, power supply, battery life, pump status, motor status, the number of protocols carried out with an MPDS 31, and the like and combinations thereof. In some embodiments, the system may be configured to provide an audible or visual warning when the system pressure drops below a minimum or rises above a maximum level. The system may also provide warnings if pump fails or the temperature in the calibration chamber or vial holding well reaches a critical level, power is lost, or other interruption in the procedure is identified. In certain embodiments, the system may automatically stop without input from the operator when critical parameters have been reached to avoid injury to the patient.

The systems of various embodiments may be configured to deliver any radiopharmaceutical known in the art, and the radiopharmaceutical may be delivered alone or in combination with another pharmaceutical composition. For example, in some embodiments, the system may be designed and configured to deliver $^{47}$Ca—Ca$^{2+}$, $^{11}$C-L-methyl-methionine, $^{14}$C-glycocholic acid, $^{14}$C-para-amino benzoic acid (PABA), $^{14}$C-urea, $^{14}$C-d-xylose, $^{51}$Cr-red blood cells, $^{51}$Cr—Cr$^{3+}$, $^{51}$Cr-ethylenediaminetetraacetic acid (EDTA), $^{57}$Co-cyanocobalamin (vitamin B$_{12}$), $^{58}$Co-cyanocobalamin (vitamin B$_{12}$), $^{169}$Er-colloid, $^{18}$F-fluorodeoxyglucose (FDG), $^{18}$F-fluoride, $^{18}$F-fluorocholine, $^{68}$Ga-dotatoc or dotatate, $^{3}$H-water, $^{111}$In-diethylenetriaminepenta-acetic acid (DTPA), $^{111}$In-leukocytes, $^{111}$In-platelets, $^{111}$In-pentetreotide, $^{111}$In-ocetreotide, $^{123}$I-iodide, $^{123}$I-o-iodohippurate, $^{123}$I-m-iodobenzylguanidine (MIBG), $^{123}$I-FP-CIT, $^{125}$I-fibrinogen, $^{131}$I-iodide, $^{131}$I-iodide, $^{131}$I-m-iodobenzylguanidine (MIBG), $^{59}$Fe—Fe$^{2+}$ or Fe$^{3+}$, $^{81m}$Kr-aqueous, $^{13}$N-ammonia, $^{15}$O-water, $^{32}$P-phosphate, $^{82}$Rb-chloride, $^{153}$Sm-ethylenediaminotetramethylenephosphoric acid (EDTMP), $^{75}$Se-selenorcholesterol, $^{75}$Se-23-Seleno-25-homo-tauro-cholate (SeHCAT), $^{22}$Na—Na$^{+}$, $^{24}$Na—Na$^{+}$, $^{89}$Sr-chloride, $^{99m}$Tc-pertechnetate, $^{99m}$Tc-human albumin, $^{99m}$Tc-human albumin macroaggregates or microspheres, $^{99m}$Tc-phosphonates and phosphate, $^{99m}$Tc-diethylenetriaminepenta-acetic acid (DTPA), $^{99m}$Tc-dimercaptosuccinic acid (V) (DMSA), $^{99m}$Tc-dimercaptosuccinic acid (III) (DMSA), $^{99m}$Tc-colloid, $^{99m}$Tc-hepatic iminodiacetic acid (HIDA), $^{99m}$Tc-denatured red bood cells, $^{99m}$Tc-red blood cells, $^{99m}$Tc-mercaptoacetyltriglycine (MAG3), $^{99m}$Tc-exametazime, $^{99m}$-sestamibi (MIBI-methoxy isobutyl isonitrile), $^{99m}$Tc-sulesomab (IMMU-MN3 murine Fab'-SH antigranulocyte monoclonal antibody fragments), $^{99m}$Tc-human immunoglobulin, $^{99m}$Tc-tetrofosmin, $^{99m}$Tc-ethyl cysteinate dimer (ECD), $^{201}$Tl—Tl$^{+}$, $^{133}$Xe in isotonic sodium chloride solution, $^{90}$Y-silicate, and the like and combinations thereof. In certain embodiments, the system may be configured for delivery of radiopharmaceuticals for imaging myocardial or other cardiovascular conditions during, for example, a stress tests. In such embodiments, the system may be configured to deliver $^{18}$F-fluorodeoxyglucose (FDG), $^{13}$N-ammonia, $^{15}$O-Water, $^{82}$Rb-Chloride, $^{99m}$Tc-pertechnetate, $^{99m}$Tc-human albumin, $^{99m}$Tc-human albumin macroaggregates or microspheres, $^{99m}$Tc-diethylenetriaminepenta-acetic acid (DTPA), $^{99m}$Tc-denatured red blood cells, $^{99m}$Tc-red blood cells, $^{99m}$Tc-exametazime, $^{99m}$Tc-sestamibi (MIBI—methoxy isobutyl isonitrile), $^{99m}$Tc-tetrofosmin, $^{201}$Tl—Tl$^{+}$, and the like and combinations thereof.

In some embodiments, the system may be configured to administer a single radiopharmaceutical composition, and in other embodiments the system may be configured to deliver two or more different radiopharmaceuticals. In embodiments in which the system is configured to deliver multiple radiopharmaceuticals, the system may allow the operator to switch configurations depending on the intended procedure. The amount of radiopharmaceutical delivered by the system may vary among embodiments and based on the protocol being used. Generally, a physician or other qualified medical personnel can determine an appropriate amount of the radiopharmaceutical to be delivered to a particular patient using metrics regarding the patient known in the art. Because of the flexibility of the system, any amount of radiopharmaceutical can be delivered.

The system may likewise be configured to deliver any other pharmaceutical composition alone or in addition to the radiopharmaceutical. For example, in various embodiments, the system may be configured to administer stress agent such as, but not limited to, IV dobutamine, IV dipyridamiole (Persantine), IV adenosine (Adenoscan), IV lexiscan (Regadenoson), and the like and combinations thereof. In other embodiments, the pharmaceutical agent may reduce vasodilation such as, for example, IV aminophylline. The amount of other pharmaceutical or stimulant delivered by the system may vary among embodiments and based on the protocol being used, and a physician or other qualified medical personnel can determine an appropriate amount of the pharmaceutical to be delivered based on patient metrics known in the art. Because of the flexibility of the system, any amount of other pharmaceutical can be delivered.

The system may be configured to deliver the radiopharmaceutical and other pharmaceutical or stimulant separately or simultaneously depending on the protocol used. For example, in some embodiments, the radiopharmaceutical may be administered to the patient followed by the administration of the other pharmaceutical or stimulant, and in other embodiments, the radiopharmaceutical and other pharmaceutical or stimulant may be administered simultaneously be the system. In still other embodiments, the other pharmaceutical may be administered and the radiopharmaceutical may be delivered at an appropriate time following administration of the other pharmaceutical. For example, in certain embodiments, a stimulant may be administered to a patient, and a radiopharmaceutical may be administered based on real time patient data such as a target heart rate, pulse, and the like. Similarly, the system may be configured to administer additional pharmaceuticals based on real time patient data. For example, if real time patient data indicates that a particular patient metric such as heart rate is too high a depressant may be administered.

Other capabilities and functions not expressly discussed hereinabove or shown in the drawings are of course conceivable in accordance with the embodiments. For example, if the extraction of a dose of the radiopharmaceutical from a vial is interrupted, the system could alert the operator to discard the dose and present a button for that purpose on the GUI.

Various embodiments are directed to methods for using the system and devices encompassed by the system. FIGS. 6-11 show schematics for some exemplary methods of the invention. The exemplary procedure provided below describes the use of a first volume (i.e., a first bolus or slug) 800 and a second volume (i.e., a second bolus or slug) 802 of a radiopharmaceutical that is delivered to a patient. This is not to be construed as limiting the injection procedure disclosed. Any suitable number of slugs may be delivered to the patient including, for example, 1, 2, 3, 4, 5, 6, and so on volumes of radiopharmaceutical. In some embodiments, the number of slugs can be increased until there is a continuous flow of radiopharmaceutical into the system. Thus, the activity of the radiopharmaceutical entering the ion chamber can be continuously measured to prepare the dose to provide a real time activity measurement as the dose is being prepared. This can be displayed to the user as it is being prepared on the GUI.

Figure 6:
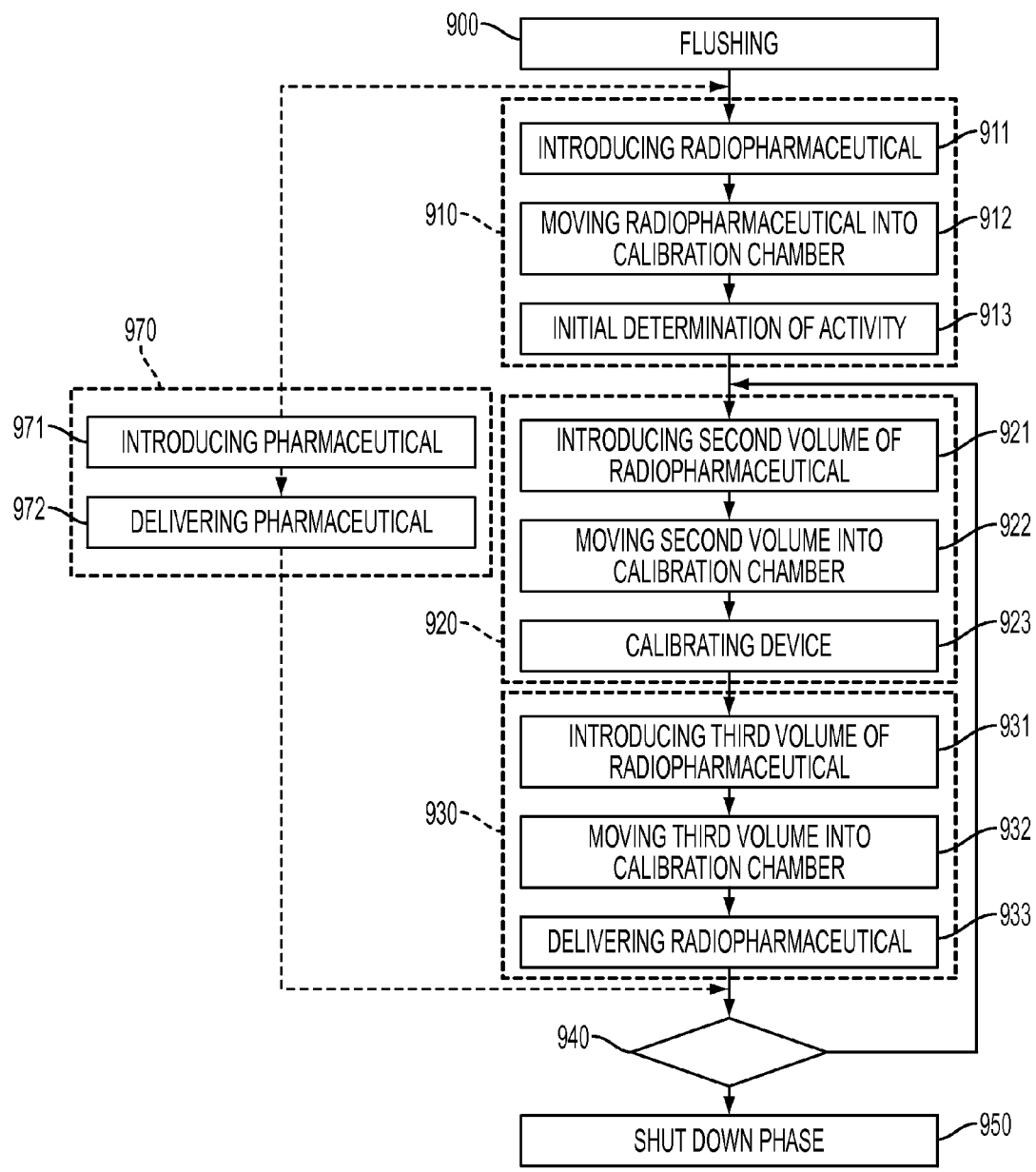
FIG. 6 is flow chart representing exemplary methods for using the radiopharmaceutical delivery system of some exemplary embodiments.

Generally, the injection procedure can be divided into five phases as represented in the flow chart of FIG. 6: 1) an initialization phase 910, 2) a calibration phase 920, 3) a delivery phase 930, 4) a procedure review phase 940 in which it is determined whether another injection shall be performed and the injection procedure is reinitiated or the injection procedure is complete, and 5) a shutdown phase 950.

In some embodiments, before starting the injection procedure, the operator may determine, i) the desired amount of radiopharmaceutical to be delivered to the patient based on the activity of the radiopharmaceutical, Ar, and ii) the estimated concentration of activity in the vial Cv (i.e., the activity per unit of volume, MBq/ml). These data may be provided to the system controller. In other embodiments, data provided to the controller may further include, the type of radiopharmaceutical provided in the system, patient information including, for example, patient name and vital statistics for the patient, the treating physician, the time of day and/or date, the type or procedure to be performed, the type of procedure and patient information for procedures to be performed before or after the procedure, the name and/or identification number of the operator, a password or other security measure, and the like and combinations thereof. The methods of various embodiments, may include the step of inputting such information before beginning the procedure. In certain embodiments, methods may further include generating a list of procedures to be performed over a time period. While the information provided in such a list may vary, in some embodiments, the list may include patient names, type of procedure, amount of radiopharmaceutical to be delivered to the identified patient, the time necessary of the procedure and/or a projected start time for the procedure, the treating physician, and the like. In particular embodiments, the information required for such a list may be inputted into the system before initiation, and in other embodiments, information for the list may be provided before the initiation of the procedure for each individual patient. In still other embodiments, information for the list may be inputted remotely, and patient information may be provided to the system via an Internet or other network connection that is hardwired or wireless.

Figure 7:
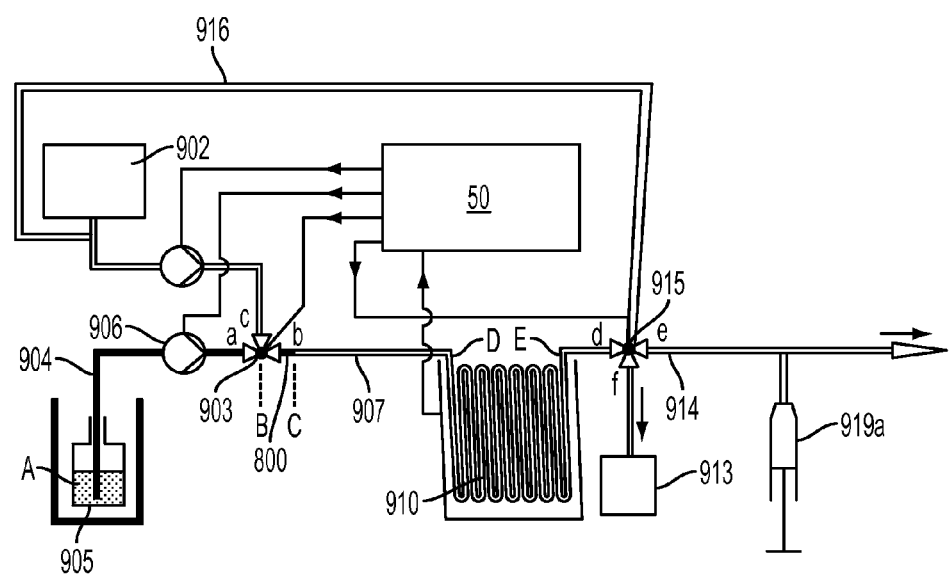
FIG. 7 is a schematic drawing showing an exemplary fluid path set during delivery of a radiopharmaceutical.

Initialization 910 may include any number of steps necessary to prepare the system for delivery of a radiopharmaceutical. In some embodiments, initialization may include the step of filling the system including all tubing and connectors with saline or another medical fluid to remove air from the fluid path set 32, i.e., flushing the system 911. As illustrated in FIG. 7, in some embodiments, the step of flushing the system may be carried out by bypassing the radiopharmaceutical 905 and associated portion of the flow path 904 by configuring the three-way valve 903 in position such that ports "c" and "b" are connected. At the same time, the four-way valve 915 can be positioned such that ports "d" and "e" are connected. Saline or another medical fluid may than be introduced into the system by injecting fluid from the reservoir 902 to point B. The three-way valve 903 may then be configured such that ports "a" and "b" are connected, while the four-way valve 915 remains configured to allow fluid to flow from port "d" through port "e." Pump 906 may then pump fluid from the radiopharmaceutical container into the radiopharmaceutical tubing section 904 until the tubing is filled from point A to point B. The three-way valve 903 may then be repositioned to connect port "c" and "d" and saline may be pumped from the medical fluid storage device 902 to a portion of the flow path beyond the four-way valve 915 through the sixth tubing section 914.

In some embodiments, the tubing section associated with the radiopharmaceutical 904 may be first flushed with saline before the radiopharmaceutical is introduced into the system. In such embodiments, saline may be pumped from a source at point A through the three-way valve 903 and four-way valve 915 before valve 903 is repositioned to allow fluid to be pumped from the medical fluid storage device 902 through the system to valve 915.

After flushing, such methods may include the step of introducing a radiopharmaceutical into the system 912 in the flow chart of FIG. 6. Returning to FIG. 7, introducing the first volume 800 can be carried out by configuring valve 903 to allow fluid flow through ports "a" and "b," while valve 915 is configured to allow flow through ports "d" and "f" thereby diverting fluid in the system to the waste receptacle. Radiopharmaceutical 905 may be introduced into the system by pumping radiopharmaceutical from vial or container at inlet point A and past point B at valve 903 to point C in the third tubing section 907 using pump 906. The volume of radiopharmaceutical between points B and C is the first volume of radiopharmaceutical 800. The actual amount of radiopharmaceutical in the first volume does not need to be known exactly so long as section of tubing from A to B is completely filled with radiopharmaceutical and the activity in the volume between B and C is not larger than the activity Ar to be administered.

Figure 8:
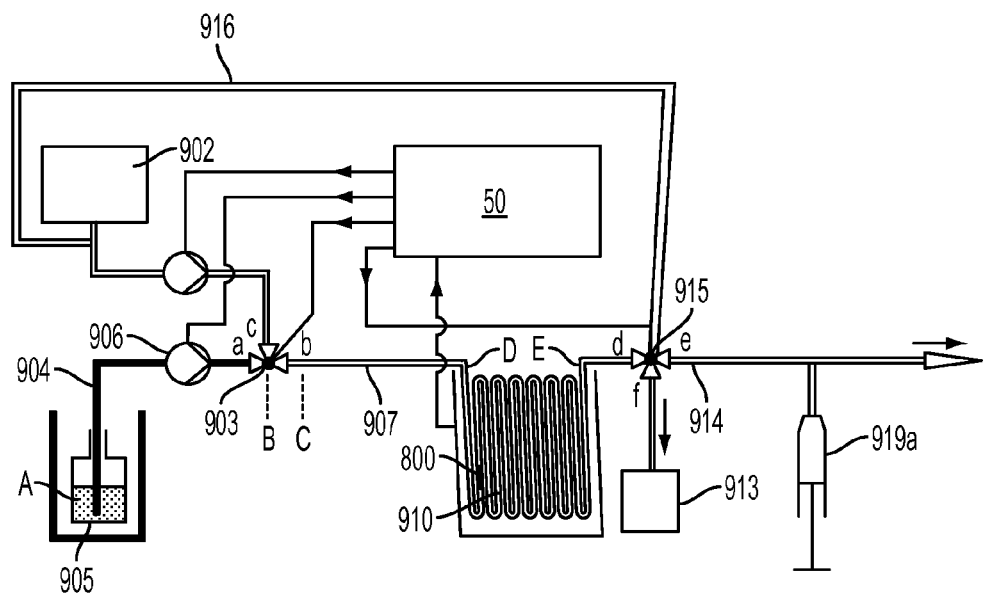
FIG. 8 is a schematic drawing showing an exemplary fluid path set during delivery of a radiopharmaceutical.

After the first volume of radiopharmaceutical 800 has been introduced into the system, it may be introduced into the ionization/calibration chamber 912 in FIG. 6 by flushing the system with additional medical fluid from the medical fluid storage device 902. This step in the method of various embodiments can be carried out by configuring valve 903 to allow flow from port "c" through port "b" and introducing a volume of saline that is slightly larger than the third tubing section 907, i.e., slightly larger than the volume between points B and D from the into the system and pushing the first volume of radiopharmaceutical 800 from the third tubing section 907 into the tube coil 910. Movement of the first volume 800 into the tube coil 910 is illustrated in FIG. 8.

After the first volume of radiopharmaceutical 800 has been introduced into the ionization/calibration chamber 910 step 912 in FIG. 6, the initial activity of the radiopharmaceutical can be determined 913. This step can be carried out by measuring the activity of the first volume of radiopharmaceutical, Al, using the radioactive emissions detectors associated with the ionization/calibration chamber. With these data, the system controller 50 may calculate the missing activity, Am, based on total desired activity, Ar, as shown in Equation 1:

$$Am = Ar - Al \quad \text{Eq. 1}$$

Figure 12:
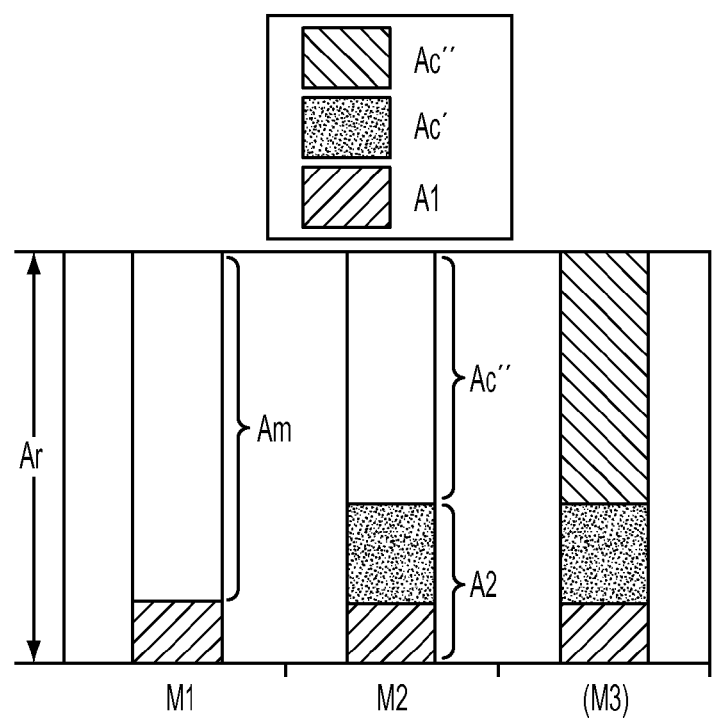
FIG. 12 is a series of bar graphs representing the delivery of a total desired amount of radiopharmaceutical.

Determination of the missing activity Am is graphically illustrated in FIG. 12 column labeled M1, indicating the first measurement.

The concentration of activity in the vial, Cv, can be inputted into the control system by the user during initialization of the system, and this value can then be used to estimate the remaining volume of the radiopharmaceutical, Vm, that should be delivered to achieve the total desired activity, Ar, as shown in Equation 2:

$$Vm = Am/Cv \quad \text{Eq. 2}$$

Figure 9:
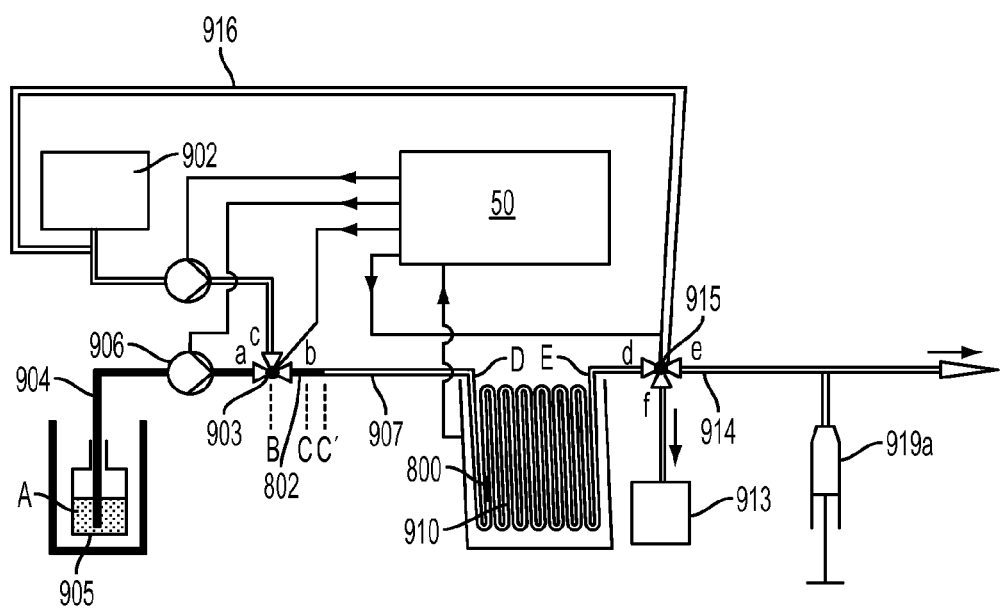
FIG. 9 is a schematic drawing showing an exemplary fluid path set during delivery of a radiopharmaceutical.

After the estimated remaining volume, Vm, has been determined, the calibration phase 920 may begin. This step is accomplished by introducing a second volume of radiopharmaceutical into the system 921. As illustrated in FIG. 9, the second volume of radiopharmaceutical 802 can be introduced into the system by switching valve 905 to connect ports "a" and "b," and pumping a second volume of radiopharmaceutical 802 into the third tubing section 907 using pump 906. The second volume 802 may fill the portion of the third tubing section to point C. Volume of the second volume of radiopharmaceutical 802 is half of the estimated missing volume, Vm, determined using Eq. 1. This volume is designated Vc' in Equation 3:

$$Vc' = Vm/2 \quad \text{Eq. 3}$$

Figure 10:
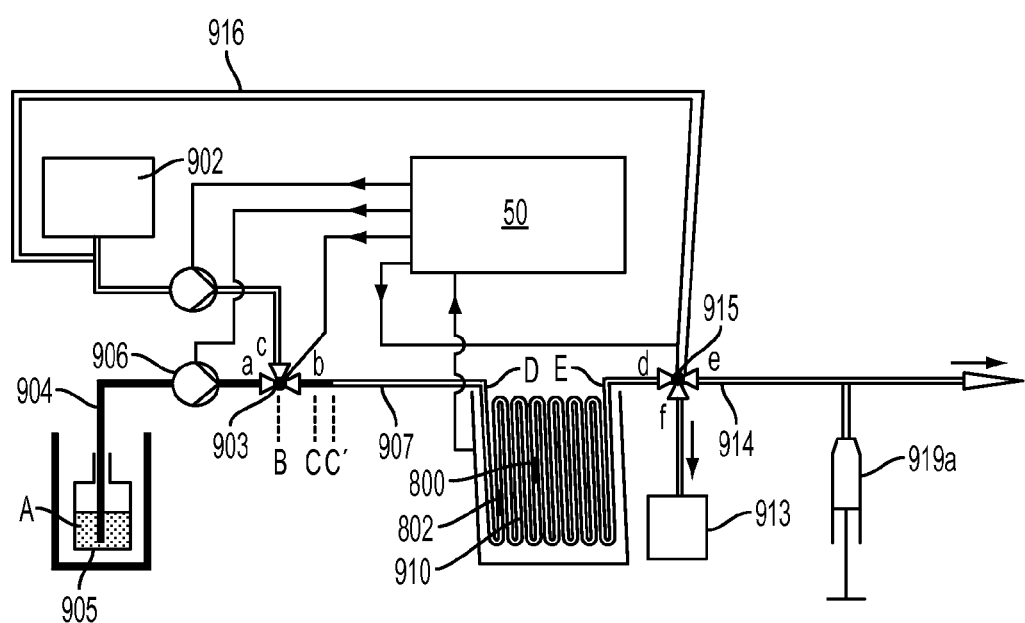
FIG. 10 is a schematic drawing showing an exemplary fluid path set during delivery of a radiopharmaceutical.

The second volume of radiopharmaceutical may then be introduced into the ionization chamber, step 922 in FIG. 6. This portion of the process may include the steps of repositioning valve 903 to connect ports "c" and "b," and pumping a volume of medical fluid into the system to move the second volume of radiopharmaceutical into the tube coil 910 as illustrated in FIG. 10.

Figure 11:
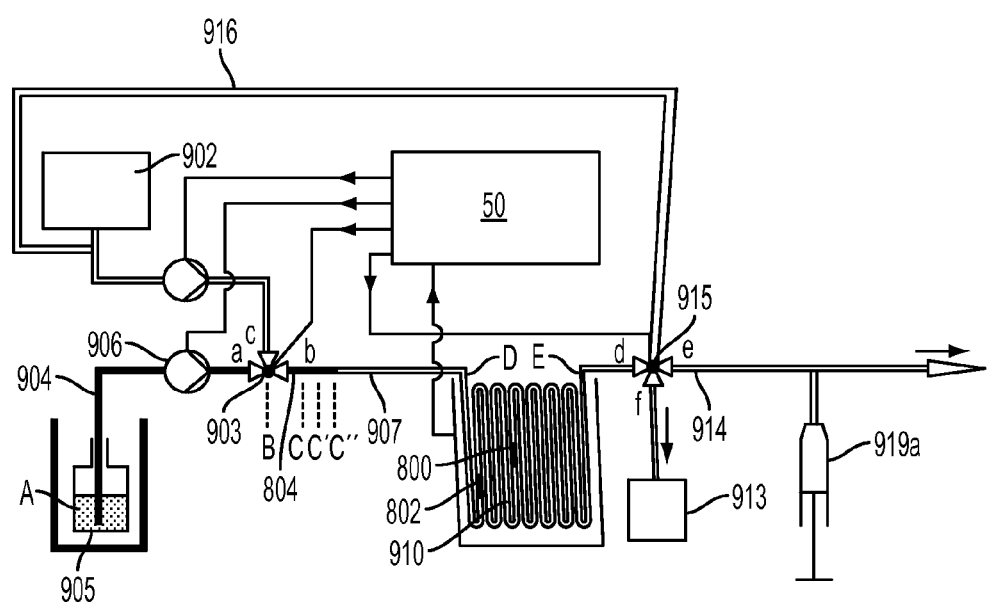
FIG. 11 is a schematic drawing showing an exemplary fluid path set during delivery of a radiopharmaceutical.

The step of calibrating the ionization/calibration chamber, step 923 in FIG. 6. This portion of the process may include the steps of measuring the radioactive emissions of the second volume of radiopharmaceutical in the tube coil 901, measurement M2, to determine the activity of the second volume of radiopharmaceutical, Ac', as illustrated in FIG. 12. As illustrated in FIG. 11, the second measurement, M2, corresponds to the radioactive emission of both the first volume of radiopharmaceutical 800 and the second volume of radiopharmaceutical 802 because both volumes are present in the tube coil 910 during the measurement. Therefore, the activity of the second volume, Ac', can be determined by subtracting the activity of the first volume A1 measured in M1 from the activity, A2, derived from the second measurement M2. The concentration of radiopharmaceutical in the vial based on the emission, Cs, can be calculated based on the amount of radiopharmaceutical, Vc', introduced into the system in the second volume of radiopharmaceutical 802, and the activity of these volume of radiopharmaceutical, Ac', as set-forth in Eq. 4:

$$Cs = Ac'/Vc' = (A2-A1)/Vc' \qquad \text{Eq. 4}$$

The system is now calibrated and can deliver an accurate dose, in mCi, of radiopharmaceutical based on the volume of radiopharmaceutical introduced into the system.

The additional amount of radiopharmaceutical required for the desired total dose Ar can be determined by determining the amount of activity Ac" required to reach a total activity of Ar as set forth in Eq. 5:

$$Ac'' = Ar - A2 \qquad \text{Eq. 5.}$$

The volume Vc" required to provide this dose of radiopharmaceutical can then calculated as set forth in Eq. 6:

$$Vc'' = Ac''/Cs = (Ar-A2)/Cs = (Ar-A2)/(A2-A1)Vc' \qquad \text{Eq. 6}$$

Having determined the correct amount of radiopharmaceutical to provide the total desired dose Ar, the delivery phase, 930, can be initiated. Delivery can include the steps of introducing a third volume of radiopharmaceutical, 804, into the system, and this portion of the process can be carried out by switching the valve 903 to connect ports "a" and "b" and pumping the volume, Vc", through valve 903 and into the third tubing section 907 to, for example, point C" as illustrated in FIG. 11. The third volume of radiopharmaceutical 804 is then introduced into the ionization/calibration chamber, step 932, by switching valve 903 to connect ports "c" and "b" and pumping a volume of medical fluid into the system sufficient to allow the third volume of radiopharmaceutical to enter the tube coil 910. In some embodiments, the total activity in the tube coil 910 can be measured (measurement M3) to confirm that the appropriate total dose of radiopharmaceutical, corresponding to the total desired activity Ar, has been introduced into the system and is prepared for delivery, and if a significant discrepancy is detected, the system can be stopped before the radiopharmaceutical is delivered. In such embodiments, the volume of the tube coil 910 must be large enough to hold all three volumes of radiopharmaceutical 800, 802, and 804. In particular embodiments, this condition can be satisfied by providing a tube coil 910 that is at least five times the volume of the third tubing section 907. In other embodiments, the third volume of radiopharmaceutical 804 may be pushed past the tubing coil for delivery without further measuring the activity of the radiopharmaceutical.

Having introduced the total desired dose of radiopharmaceutical, Ar, into the system, the radiopharmaceutical can be delivered to the delivery tube set, step 933. Delivery can be effectuated by positioning valve 915 to connect ports "d" and "e" and pumping at least a volume of medical fluid from the medical fluid storage device equal to the volume of the tube coil 910 and the delivery tube set 914 into the system. Thus, all liquid in the tube coil 910 can be flushed to the patient, and exactly the required dose of radioactivity is delivered to the patient.

In various embodiments, the method presented above may further include the step of delivering a dose of a pharmaceutical agent to the patient, step 960. This step can be carried out at any point in the process and may include the steps of introducing a volume of pharmaceutical agent sufficient to illicit the desired effect, and delivering the pharmaceutical agent to the patient. In some embodiments, the amount of pharmaceutical agent to be delivered can be determined by a physician or other medical professional. This amount can be provided in a single use syringe 919a provided with an appropriate volume of pharmaceutical agent for delivery to a single patient. In such embodiments, the system may be configured to depress the plunger completely when the step of delivering the pharmaceutical agent is initiated. In other embodiments, the amount of pharmaceutical agent may be provided in a multiuse syringe including a sufficient amount of radiopharmaceutical to be delivered to more than one patient. In such embodiments, a motor, for example, may be used to discharge an appropriate amount of pharmaceutical agent for each individual patient. The user can control the amount of radiopharmaceutical administered by controlling the motor, or providing instructions to the control system to discharge an appropriate amount of pharmaceutical agent.

The pharmaceutical agent can be introduced into the system at any point within the flow path. For example, in some embodiments, the pharmaceutical agent may be introduced into the SPDS at either the proximal or distal end of the delivery tube, and in other embodiments, the pharmaceutical agent can be introduced into MPDS either before or after the tube coil. As illustrated in FIG. 6, the step of introducing the pharmaceutical agent into the system may be carried out after flushing the system 901 and before the radiopharmaceutical delivery procedure has been initiated or the step of introducing the pharmaceutical agent into the system can be carried out after the radiopharmaceutical has been delivered to the patient and before the system is shut down. In still other embodiments, the pharmaceutical agent can be introduced into the system simultaneously with the radiopharmaceutical and both compositions can be delivered to the patient at the same time.

In some embodiments, another injection of the radiopharmaceutical and/or another injection of pharmaceutical agent may be delivered to the same or a different patient. In such embodiments, procedure may continue by repeating the delivery phases 930 alone, or the calibration phase 920 and delivery phase 930 when additional radiopharmaceutical is required, and/or the pharmaceutical agent delivery phase 960, when additional pharmaceutical agent is required. In various embodiments, the initialization phase 910 may not be repeated, since the tube coil 910 has been flushed with saline, and the radiopharmaceutical extends to point B. Moreover, because no activity is present in the coil section 410, A1, in the above calculations, can be set to zero, and Am and Ar are equal. In the event that no further injections are necessary, the procedure maybe terminated using a shutdown protocol, which may include one or more steps of flushing system with a medical fluid.

The systems, methods, and devices described above may include a number of inherent safety features. For example, redundancy in the operation of the device may reduce the possibility that more than the desired dose of radiopharmaceutical will be delivered to the patient, even in the event of failure of one component, such as a pump or a valve. In particular, only the dose of radiopharmaceutical in the tube coil 910 will be delivered to the patient because there is no direct connection from the vial 902 and the fluid delivery set. Additionally, sequential measurement of activity within the tube coil 910 allows the radioactive dose of radiopharmaceutical to be determined before the complete dose is introduced into the system. Thus, measurement M3 confirms that the correct amount of radiopharmaceutical is present in the tube coil 910 before the radiopharmaceutical is delivered. If significant discrepancies are detected between the expected result and the actual measurement, procedure can be terminated, and/or the user will be notified of the discrepancy using, for example, an audible or visible alarm.

In some embodiments, no radiopharmaceutical will enter the waste reservoir 313 thereby minimizing the generation of radioactive waste.

The methods described above may include any number of additional steps including, for example, replacing the MPDS 31, placing the waste receptacle into the waste receptacle well, placing tube coil into ionization/calibration chamber, placing tubing into operative connection with pump, placing the tubing into operative connection tubing holder, placing a spike or cannula into fluid connection with radiopharmaceutical source or vial, placing tubing into operative connection with pinch valve, and placing tubing into operative connection with air detectors, mounts, and other devices, hanging a medical fluid source on a hook, mounting on fluid delivery system, and combinations thereof. The method may further include priming the system by flushing with medical fluid, connecting the SPDS with the MPDS, priming the SPDS to provide a wet connection at the patient end.

Additional embodiments are directed to a method for estimating the flow rate of the device using, for example, flow rate sensors, pressure sensors, or the change of activity (slope) of the radiopharmaceutical. In embodiments in which the activity of the radiopharmaceutical is used to determine flow rate, a known volume of the radiopharmaceutical can be pumped into the and out of the ionization/calibration chamber by pumping additional fluid into the third and fourth tubing sections. The activity of the radiopharmaceutical in the ionization/calibration chamber can be measured repeatedly during this process and a slope of the radioactive emissions can calculated from the measured activity values over time. Based on the slope of the emitted radiation and the volume of the ionization/calibration chamber, the average rate at which the radiopharmaceutical is replaced by saline can be calculated which corresponds to the flow rate of the fluid is in the device. Because the radiopharmaceutical and chamber materials may be chosen such that radioactive emissions from the radiopharmaceutical penetrate the walls of the ionization/calibration chamber before being measured, it is possible to measure the flow rate of the fluid without placing mechanical measuring devices in the fluid stream. Similarly, the flow rate of a radiopharmaceutical to a patient and the location of the radiopharmaceutical within the MPDS 31 can be determined. In particular, the activity in the chamber ($A_c$) in the ionization chamber and activity in the tubing ($A_t$) at the beginning of the procedure can be measured directly. Based on these data, the activity per unit concentration (e.g., MBq/ml) can be determined for the vial as a whole. In some embodiments, the decay rate for the radioactive tag can be used to determine the activity of the radiopharmaceutical remaining in the vial. In still other embodiments, the total time for the infusion attempt, and the volume of tubing between the ionization chamber 310 and the end of the patient line can be used in conjunction with the data described above to determine precisely the amount of radiopharmaceutical administered to the patient.

Once the average flow rate of the radiopharmaceutical through the MPDS 31 is determined, this information can be used to determine the location or distribution of the first volume of radiopharmaceutical 800, the second volume of radiopharmaceutical 802, and/or the third volume of radiopharmaceutical within the system. Additionally the average flow rate along with fluid mechanical properties of the tubing such as diameter and surface treatment, can be used to determine the location of the leading edge and the trailing edge of the radiopharmaceutical volume. By knowing the location of the radiopharmaceutical within the fluid path set 32, system parameters can be adjusted to ensure that the injection is fully completed and the radiopharmaceutical dose and pharmaceutical agent are completely administered.

Shown schematically in FIG. 13-23 are examples of a touch screen displays for the GUI 15, that can be employed with the fluid delivery system 10. As a non-restrictive example, such a touch screen arrangement could be utilized in conjunction with the system controller 50 and/or computer 1000, 1044 of any of a variety of fluid delivery systems as broadly contemplated herein. To clearly and unambiguously communicate to an operator the current status of the fluid delivery system 10, a GUI 15 with easily legible symbols and icons, including operator-friendly data entry mechanisms can be used. While a touch screen is described in these embodiments, other types of data entry devices can be used to achieve an equivalent purpose, for example, soft or hard key entry, trackball, mouse, a cursor control touch pad, and the like a separate computer system that provides data or instructions via a network or internet connection.

Figure 13:
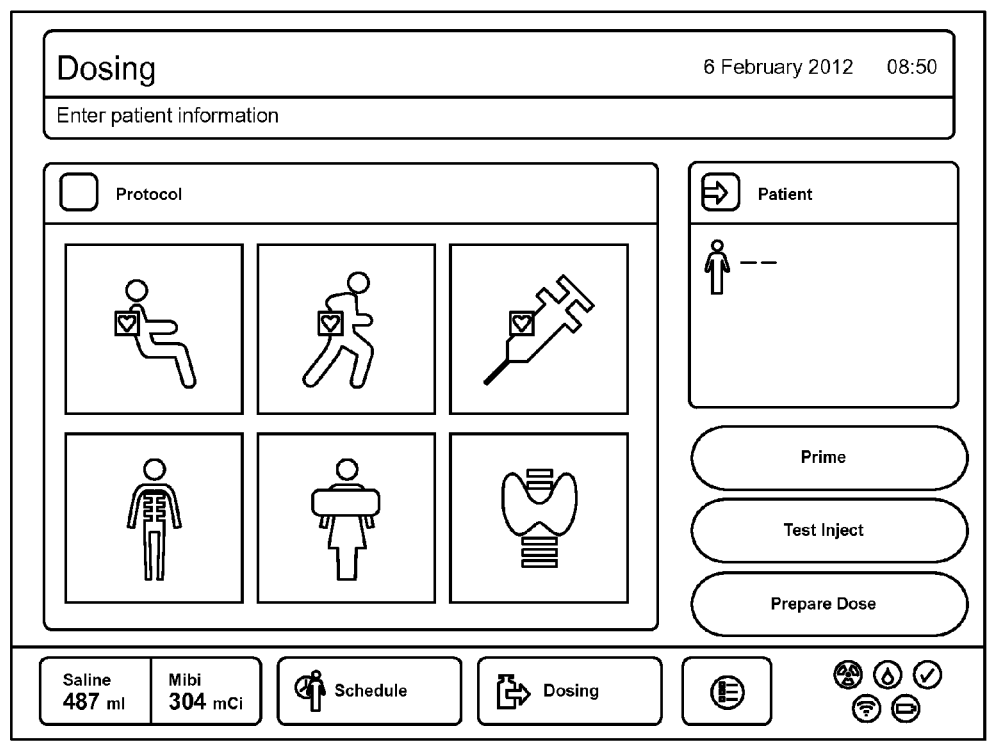
FIG. 13 is screen shot representing an exemplary main operator interface.
Figure 14:
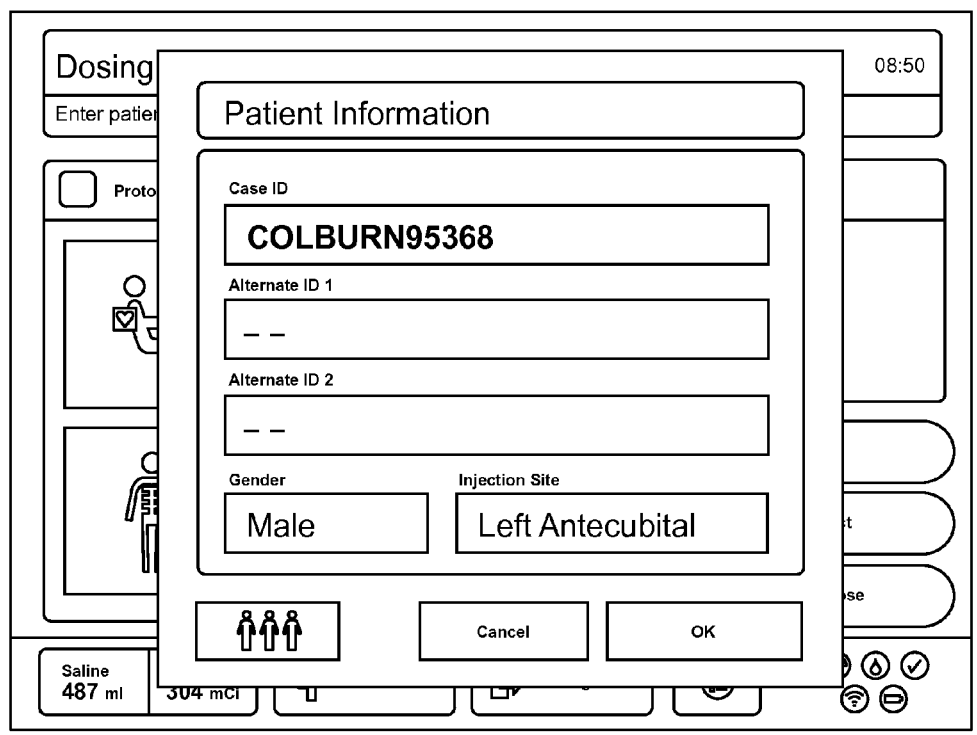
FIG. 14 is screen shot representing an exemplary pop-up window configured for entry of patient information.
Figure 15:
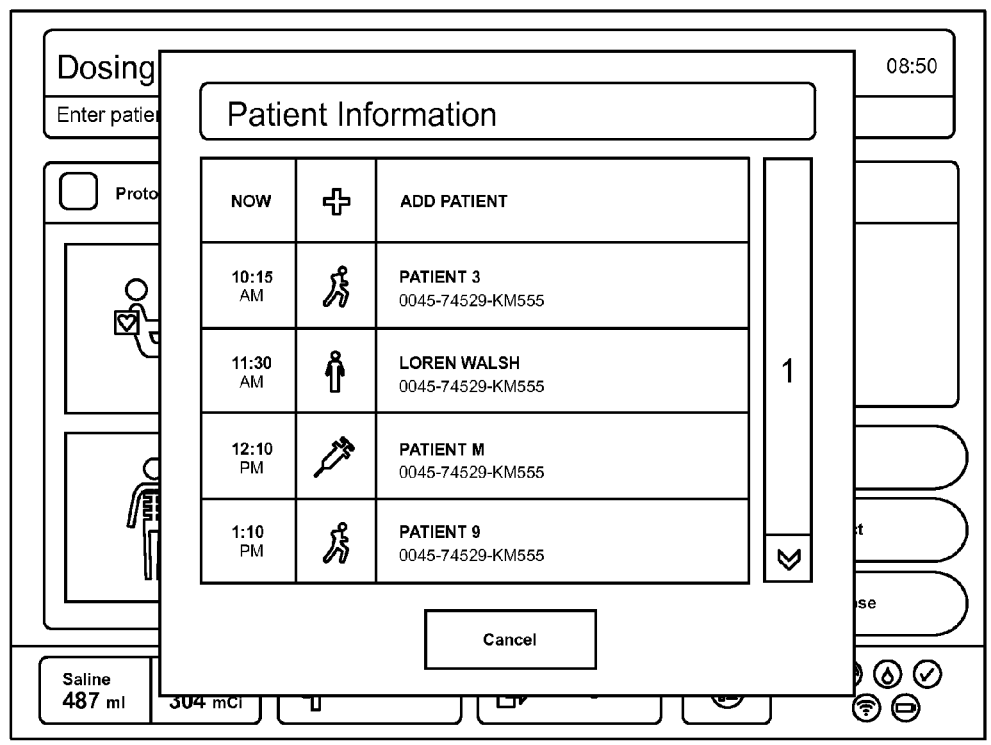
FIG. 15 is screen shot representing an exemplary pop-up window showing a patient schedule.

FIG. 13, a main operator interface provided on a touch screen is illustrated before an injection procedure has been started. The interface may provide any amount or type of data and may prompt the user to begin the procedure in any way. For example, in some embodiments, the user may be prompted to select a button for providing a schedule of procedures, which will bring up a list of patients scheduled to be administered radiopharmaceutical during the course of a defined period of time such as, for example, a 8 hour, 10 hour, 12 hour, or several day long period, as illustrated in FIG. 15. In some embodiments, the user may select a patient and begin entering relevant patient data as prompted by the system, and in other embodiments, as illustrated in FIG. 13, the user may be prompted to begin the procedure by entering patient information. In such embodiments, after activating an enter patient information button, a window listing necessary patient information may appear, as illustrated in FIG. 14. Such patient information may include, but is not limited to, patient name or ID number, case ID number, treating physician name or ID number, the type or procedure to be performed, gender, weight, height, location of injection for delivery, and the like. The user can enter relevant information using a touch screen keypad or a keypad provided with the system. After patient information is entered, a second window may appear, as illustrated in FIG. 15, that provides a schedule of patients that includes the patient whose information was entered. In certain embodiments, the patient data may be accessed using, for example, an RFID or bar code associated with the patient. For example, in some embodiments, the system may further include a bar code reader that is positioned to scan a bar code on a patient wristband. The user may scan the bar code on the patient wristband and the system will automatically access the proper protocol for that patient even if the patient is entered out of turn.

Figure 16:
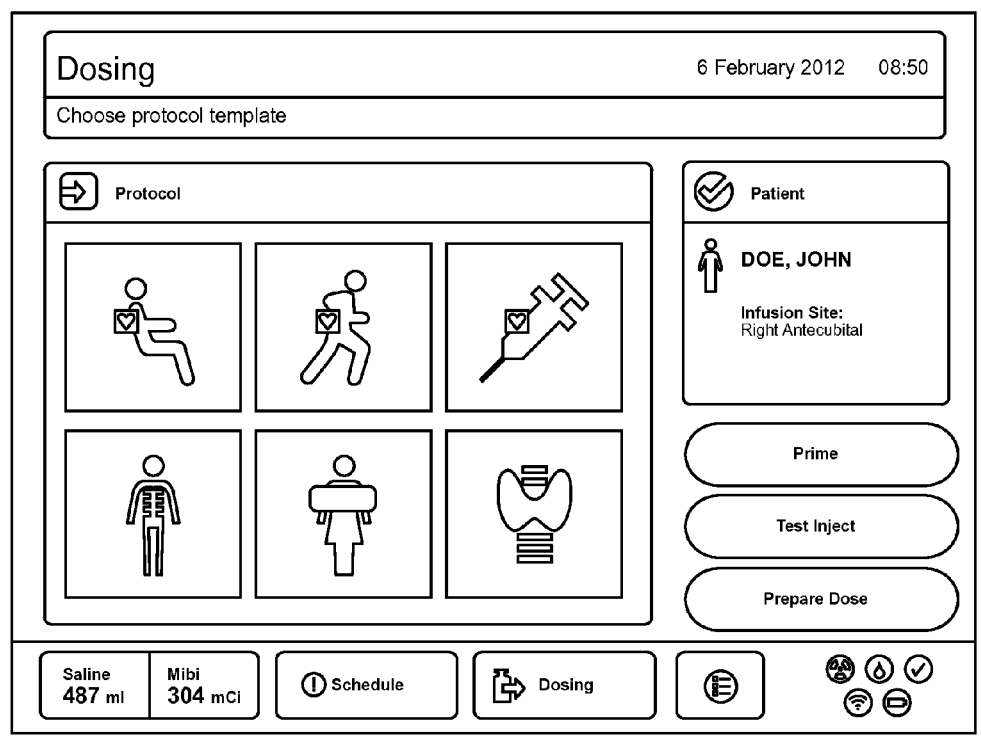
FIG. 16 is screen shot representing an exemplary dosing protocol selection screen.

The system may return to the main operator interface that includes a window including patient information for the next scheduled patient as illustrated in FIG. 16. The user may be prompted to choose a protocol to be carried out by selecting an icon. In other embodiments, the protocol can be entered when the patient information is entered into the schedule. In that case, the protocol does not need to be selected here, and the user will be prompted to move directly to the screen provided in FIG. 17. The pre-entered protocol can be overridden at any time by pressing the "Protocol" button. This will take the user back to the protocol selection screen and a new protocol can be selected by choosing the appropriate icon. Icons associated with the main operator interface may include a list of protocols that can be carried out either graphically, using images, alphabetically, using words, numerically, or combinations thereof. For example, FIG. 16 shows graphical icons for protocols including a cardiac rest procedure (a), a cardiac stress test with exercise (b), pharmaceutically induced cardiac stress test (c), bone scan (d), breast scan (e), and thyroid scan (f).

Figure 17:
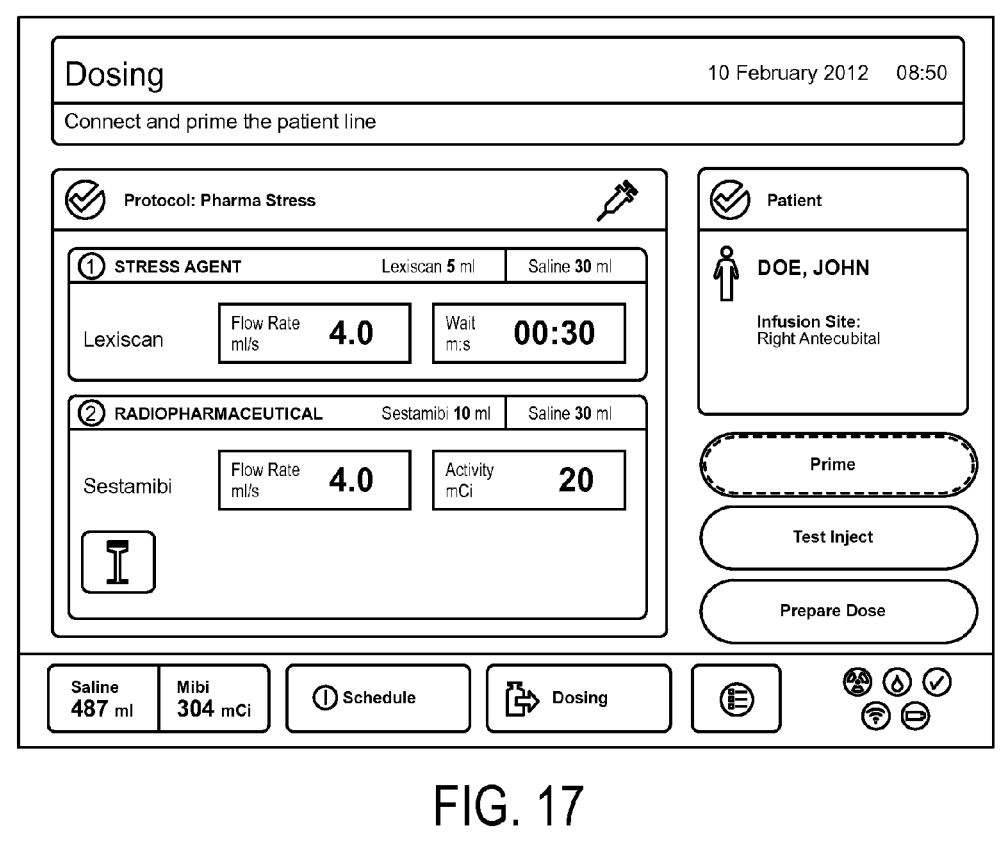
Figure 18:
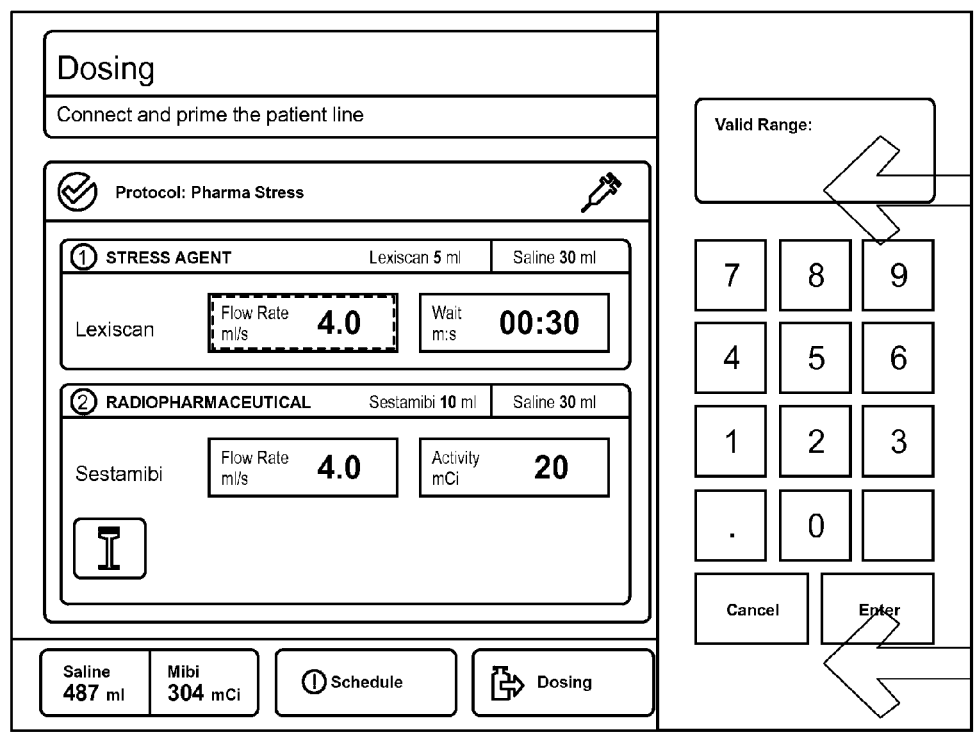
FIG. 18 is screen shot representing an exemplary pop-up window providing a key pad for entry of dosing information into fields in the dose delivery input screen.

Following selection of a protocol, a window prompting a user to connect and prime the patient line, as illustrated in FIG. 17, may appear. In some embodiments, patient information may be displayed in this window that includes infusion site. Additional information may also be displayed including, for example, the flow rate and time of delivery for a stressor, Lexiscan in FIG. 17, and a flow rate and amount of activity of radiopharmaceutical to be delivered during the protocol. In some embodiments, the information displayed may be general procedural conditions, and in other embodiments, the information displayed may have been inputted with the patient data in the screen described above. In still other embodiments, the window may be configured to be manipulated by the user such that, for example, a flow rate and time for delivery of stressor can be inputted directly into the screen. FIG. 18 provides an illustrative embodiment of a pop-up window that appears when the user changes a manipulateable variable.

Figure 19:
FIG. 19 is screen shot representing an exemplary dosing delivery input screen including fields for entry of patient information for delivery by patient weight dosing.
Figure 20:
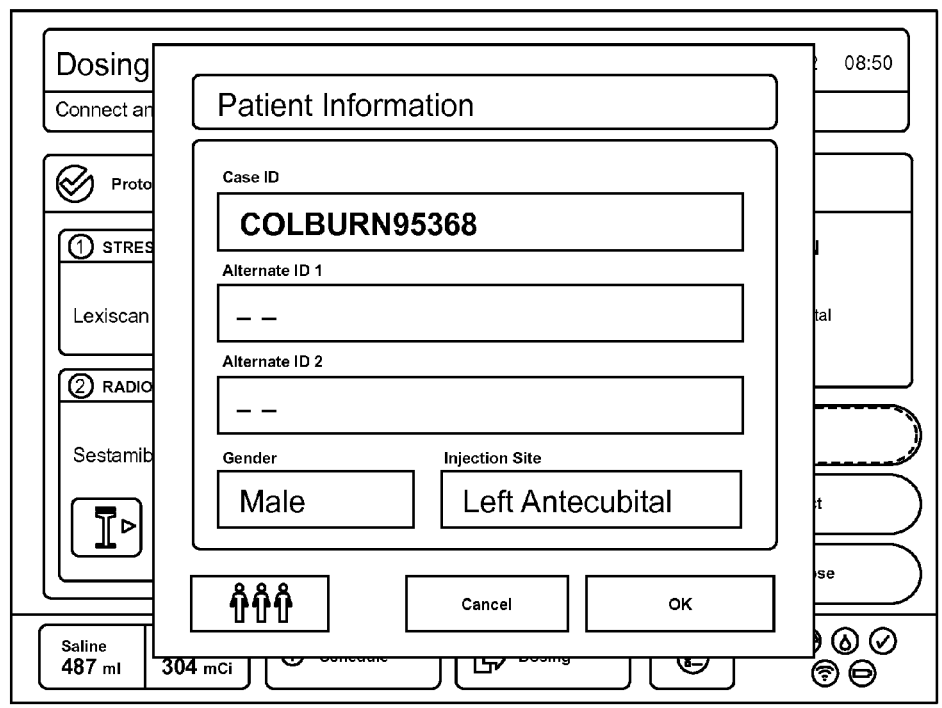
FIG. 20 is screen shot representing an exemplary pop-up window for entry of patient data used in connection with dosing delivery.

In some embodiments, as illustrated in FIG. 19, the amount of radiopharmaceutical delivered to the patient may be based on, for example, the weight of the patient (mCi/lbs). In other embodiments, another physiological factor such as body mass index (mCi/BMI), blood glucose (mCi/mg/dL), and the like can be used to determine the dosage. In embodiments in which weight is used, the user may be prompted to enter the patient's weight into an appropriate box on the screen, or the user may select an icon, such as the scale provided in FIG. 19, which will cause a pop-up screen including patient information to be brought up where the user can provide the patient's weight (FIG. 20). When the patient's weight has been inputted, the amount of activity and/or flow rate may automatically adjust to provide the correct amount of radiopharmaceutical to be delivered. Once all patient data has been inputted, the system may be configured to prompt the user to carry out the steps of preprogrammed protocols such as those identified above, namely, protocols including a cardiac rest procedure (a), a cardiac stress test with exercise (b), pharmaceutically induced cardiac stress test (c), bone scan (d), breast scan (e), and thyroid scan (f).

In some embodiments, the MPDS can be installed and primed at the beginning of the day before any protocols are selected. In such embodiments, the setup (Supply) buttons may allow the user to navigate to the screen where the MPDS is installed, and radiopharmaceutical assay information and saline volume is entered. This screen may further include an MPDS "Prime" button that once depressed instructs the system to carry out the MPDS priming procedure.

Figure 21:
FIG. 21 is screen shot representing an exemplary dosing delivery input screen during priming.

While the protocol window is displayed (FIG. 19), the user may connect the SPDS to the system and prepare the system to be primed. Here, priming may include the steps of, for example, checking medical fluid, radiopharmaceutical, and pharmaceutical agent levels or inserting any of these materials into the system. If any of the fluid levels are low, the system may prompt the user to refill. When the levels are sufficient, the system may allow the user to then contact the "Prime" button to begin the procedure. The screen may indicate that the system is priming, and in some embodiments, a progress bar may be provided on the screen to allow the user to monitor the time necessary for the priming procedure, as illustrated in FIG. 21.

Figure 22:
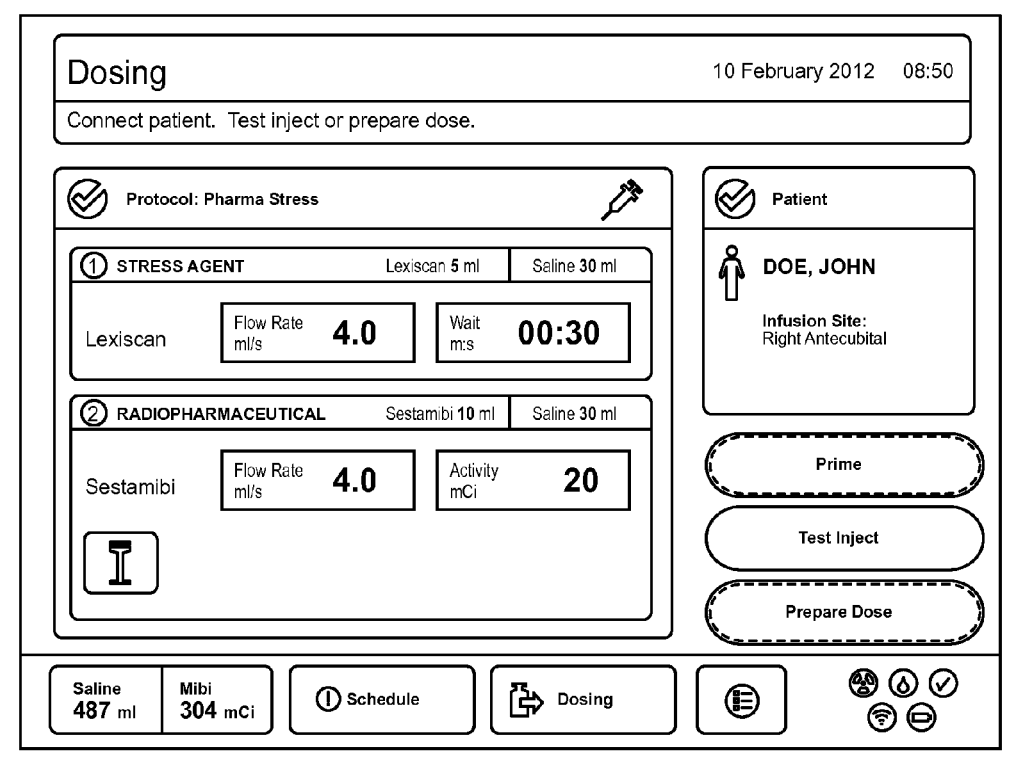
Figure 23:
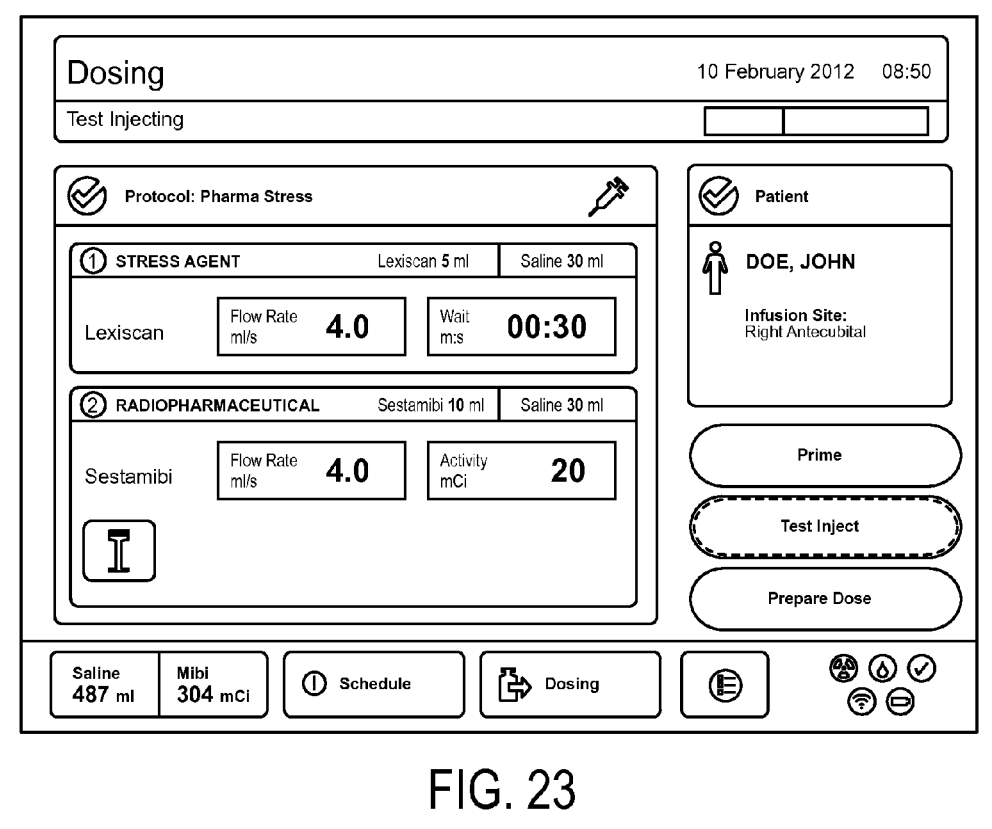
Figure 24:
FIG. 24 is screen shot representing an exemplary dosing delivery input screen after completion of saline test injection.

After the priming protocol has been completed, the user may be prompted to connect the patient to the system as indicated in FIG. 22, and the user may be prompted to prepare or inject a dose or perform a test injection to ensure that the system is functioning properly. In some embodiments, a pressure graph may appear as the test injection is carried out providing a means for the user to visually verify that the test injection results in acceptable delivery pressure. Buttons provided on these screens may allow the user to choose the proper procedure. As illustrated in FIG. 23, when test inject is selected, the screen may be modified to indicate that the test injection protocol is underway and a progress bar may be provided, pressure graph, or other means for tracking the procedure or combination of tracking means may be provided. The system may indicate when the test injection protocol is completed either by indicating that the test injection is complete or prompting the user that the system is ready to measure a dose of radiopharmaceutical. A button for preparing a dose may further be highlighted, as illustrated in FIG. 24. In certain embodiments, the test injection step may be omitted, and the user may select the "Prepare Dose" button without first performing a test injection.

Figure 25:
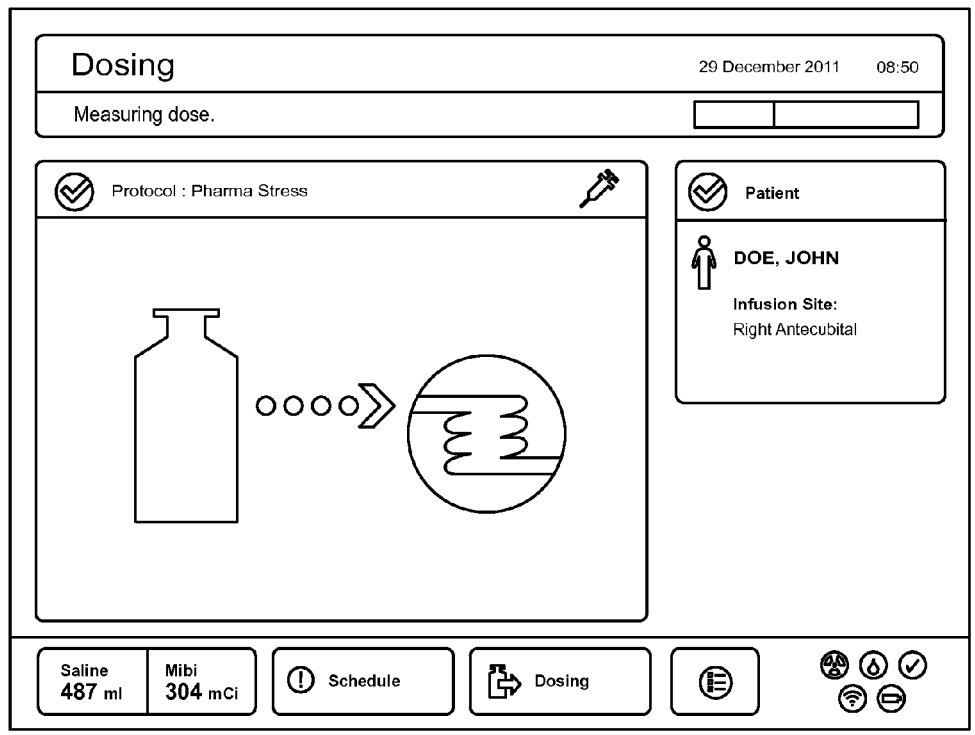
FIG. 25 is screen shot representing an exemplary dosing delivery input screen showing the progress of radiopharmaceutical dose measurement.
Figure 26:
FIG. 26 is screen shot representing an exemplary dosing delivery input screen prior to dose injection of the stress agent.
Figure 27:
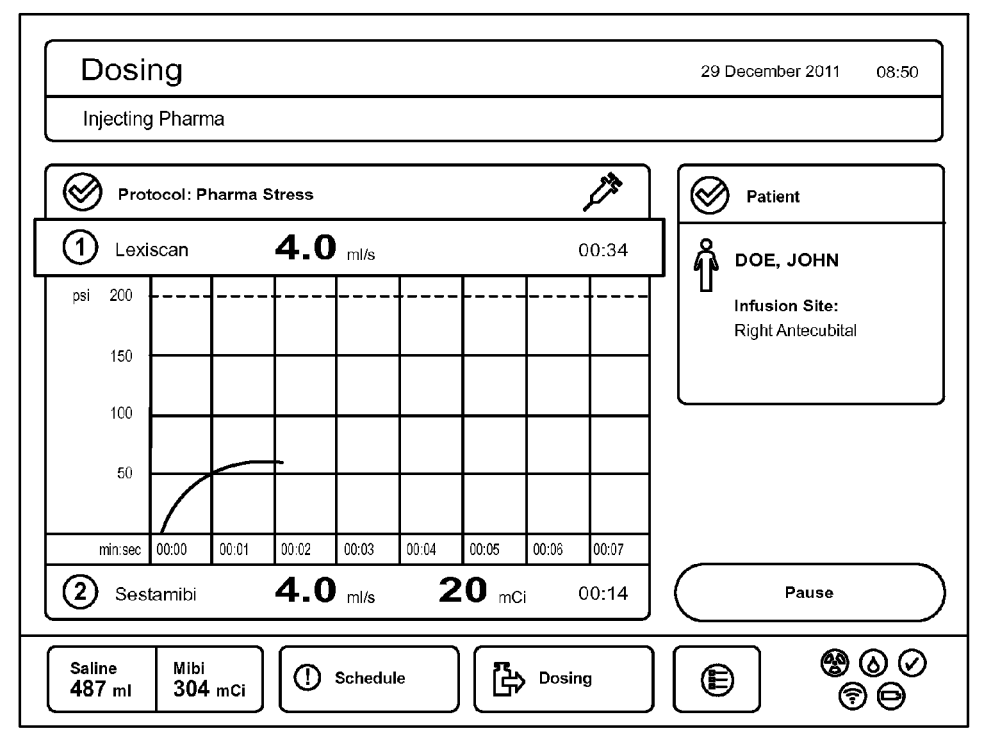
Figure 28:
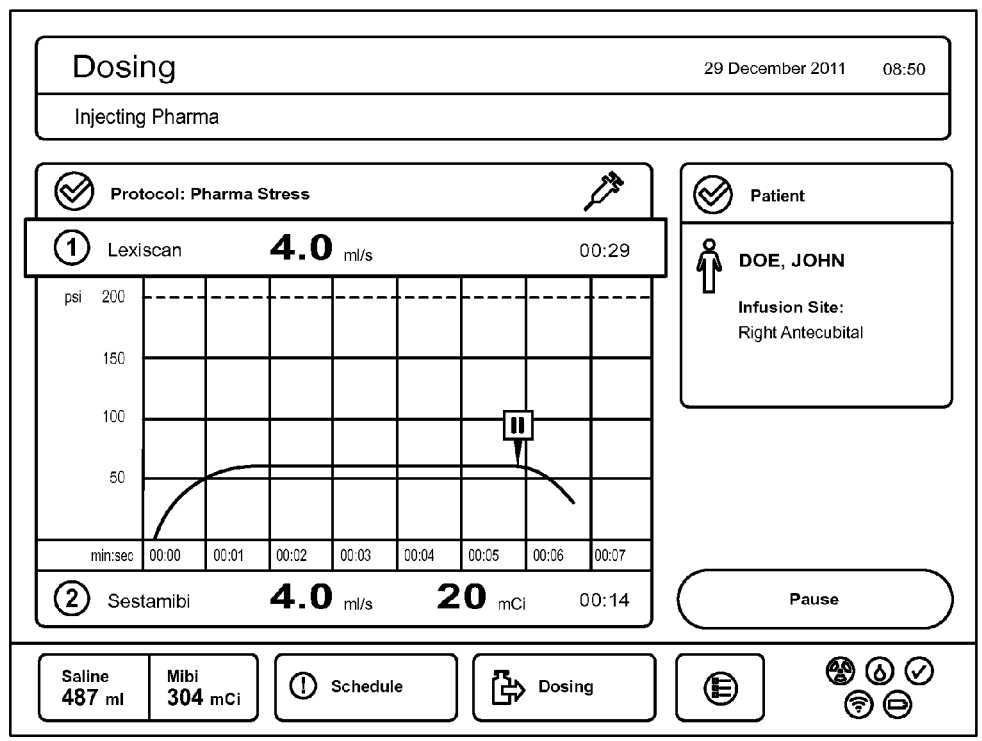
FIG. 28 is screen shot representing an exemplary dosing delivery input screen when the dosing protocol is paused.

In some embodiments, the protocol window may remain in place and a progress bar may be introduced indicating that a dose is being measured and the time period remaining before the dose has been measured when the prepare dose button is activated. In other embodiments, a screen illustrating the procedure and a progress bar, as illustrated in FIG. 25 may be brought up, which shows the progress of the dose measurement. When dose measurement is complete another window may appear that prompts the user to inject or discard the dose. As illustrated in FIG. 26, in some embodiments, the window may indicate that the dose is ready to inject and may provide a means for tracking the delivery of the dose such as, for example, a progress bar or a graph configured to show the change in a variable that results from the injection of the pharmaceutical agent. For example, as illustrated in FIG. 26, the change in pressure (psi) in the system may change over time when the pharmaceutical agent is introduced into the system. FIG. 27 shows a screen shot of the screen during introduction of the pharmaceutical agent and the progress of the protocol as indicated by the change in pressure of the system. The amount of pharmaceutical agent delivered in real time may also be presented on this screen as well as the time remaining in the procedure. The screen may further include a pause button. FIG. 28 shows a screen shot taken further into the procedure after delivery of the pharmaceutical agent is almost complete.

Figure 29:
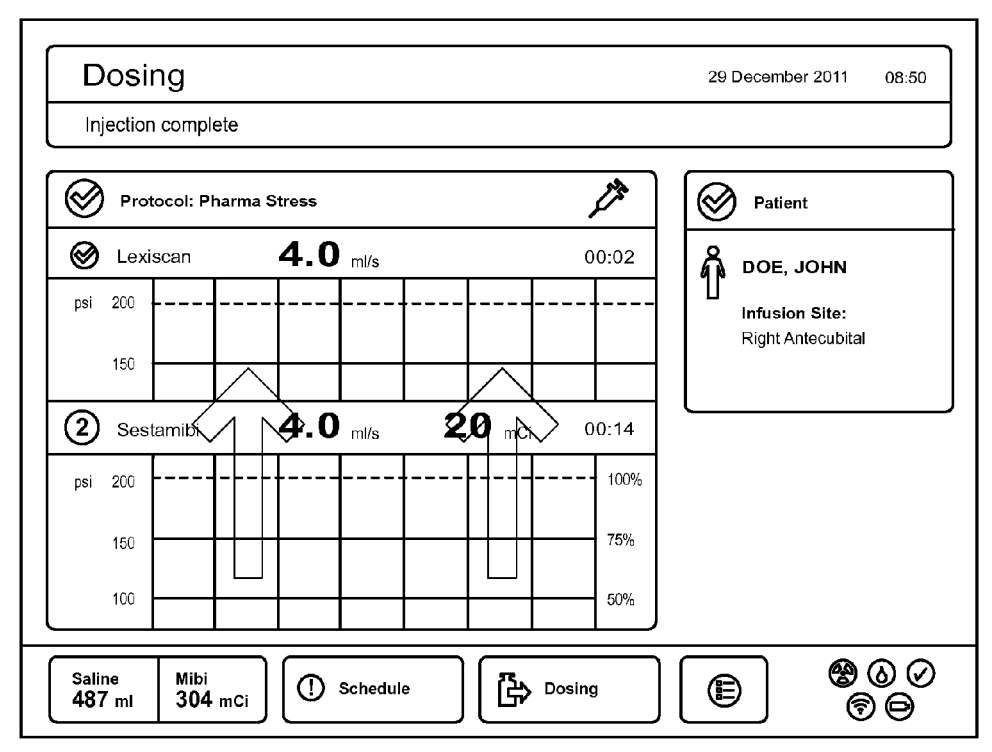

FIG. 29 shows a screen shot after completion of delivery of the pharmaceutical agent. In some embodiments, the system may provide an indication that administration of the pharmaceutical agent is complete. For example, a checkmark is provided next to Lexiscan in the exemplary screen shot provided in FIG. 29. A screen indicating that the system is preparing to deliver the radiopharmaceutical may be brought up or otherwise moved into position indicating that the system is prepared for radiopharmaceutical delivery.

Figure 30:
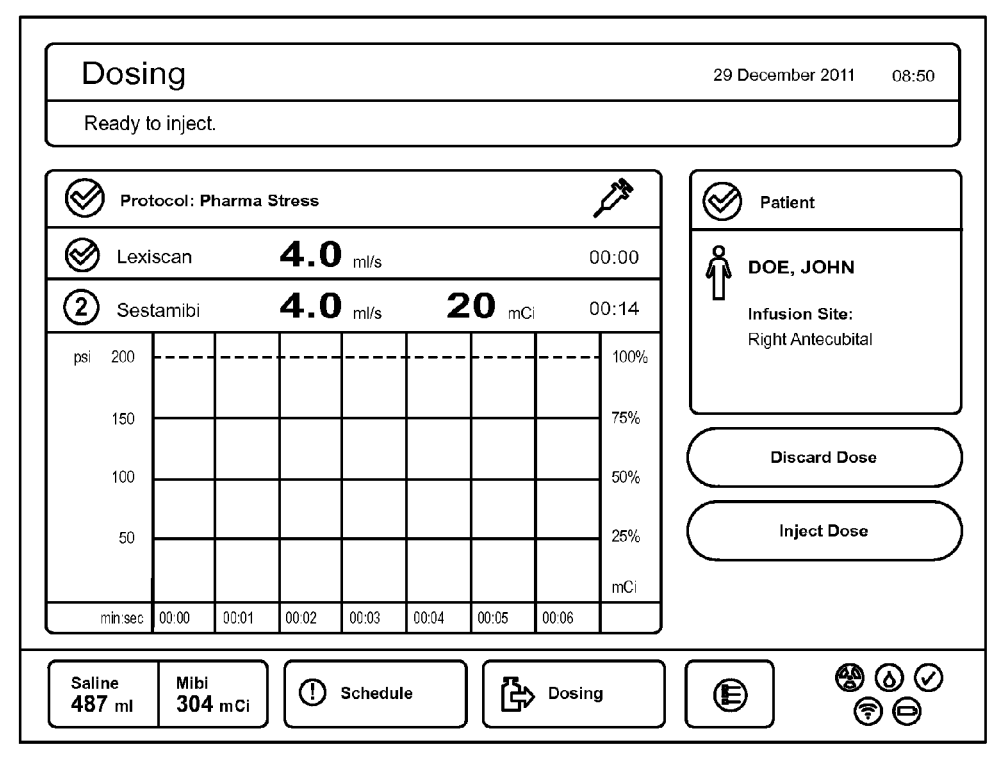

In some embodiments, the system may automatically begin injection of the radiopharmaceutical after delivery of the pharmaceutical agent is complete. In other embodiments, a screen such as that presented in FIG. 30 may appear which prompts the user to inject the dose of radiopharmaceutical by, for example, indicating that the system is ready to inject. In some embodiments, the system may include a stopwatch function that shows how long it has been since the stimulant was injected. The user can initiate the radiopharmaceutical injection after the correct amount of time has passed via the GUI, a hand switch (cable or wireless), or foot switch (cable or wireless). In other embodiments, the radiopharmaceutical may begin injection automatically after a programmed time has elapsed from the injection of the stimulant. In some embodiments, the time period may be a pre-programmed time period and in other embodiments, the user can program injection of the radiopharmaceutical after a specific time period, for example, 20 seconds after the stimulant injection is completed.

Figure 31:
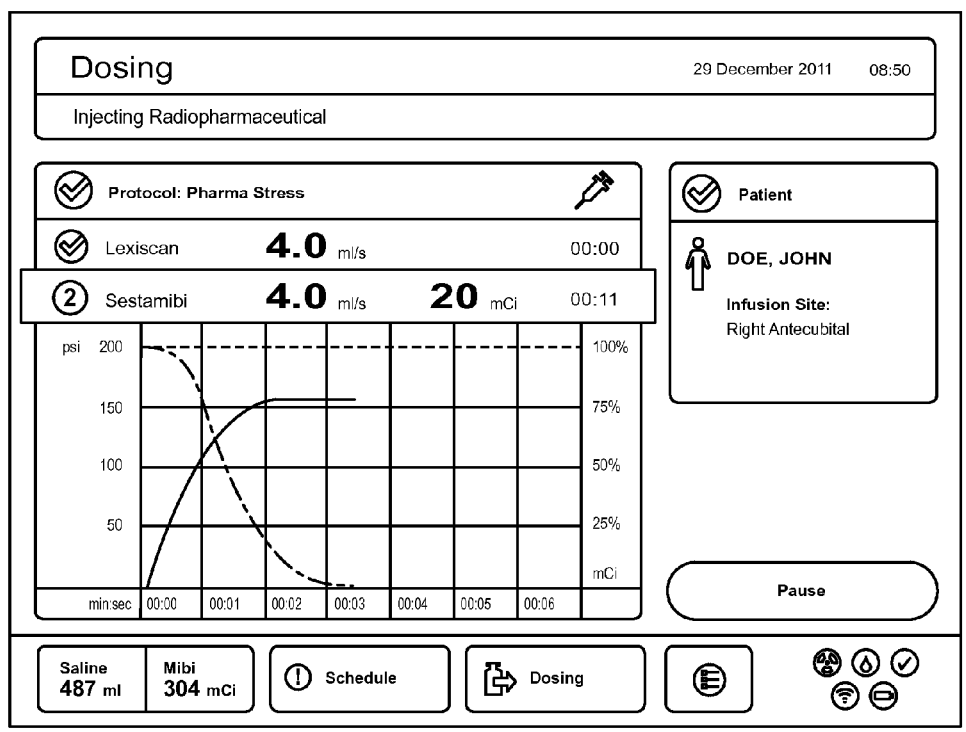
FIG. 31 is screen shot representing an exemplary dosing delivery input screen indicating the progress of radiopharmaceutical injection.
Figure 32:
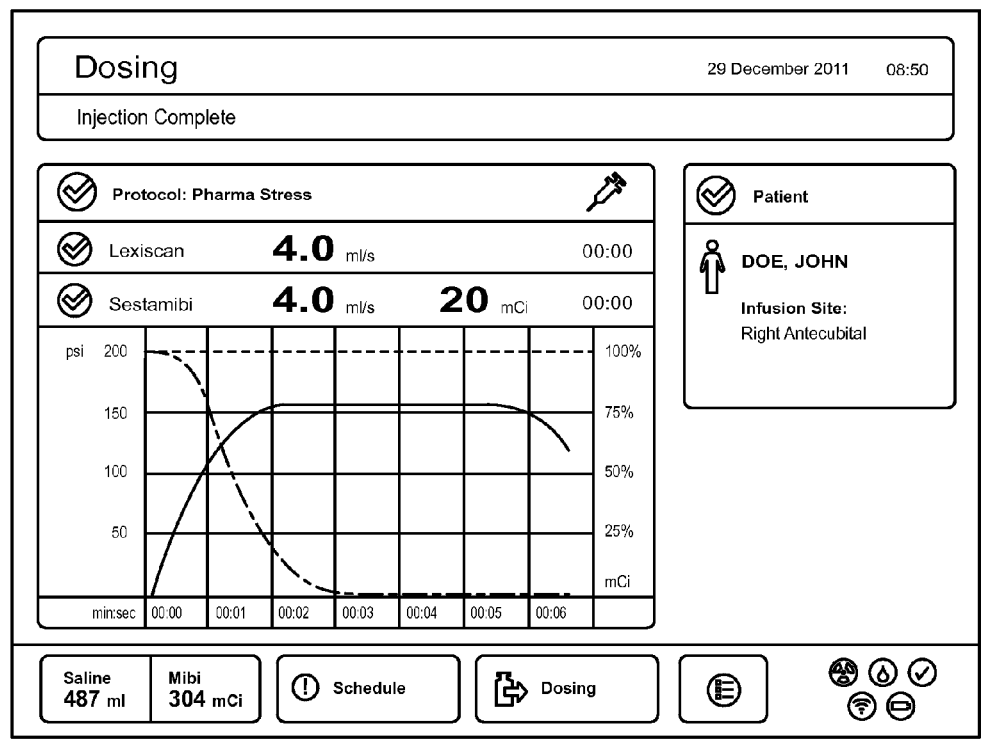
FIG. 32 is screen shot representing an exemplary dosing delivery input screen when the radiopharmaceutical injection is almost complete.
Figure 33:
FIG. 33 is screen shot representing an exemplary window upon completion of the dosing protocol showing the summary of the dosing protocol.
Figure 34:
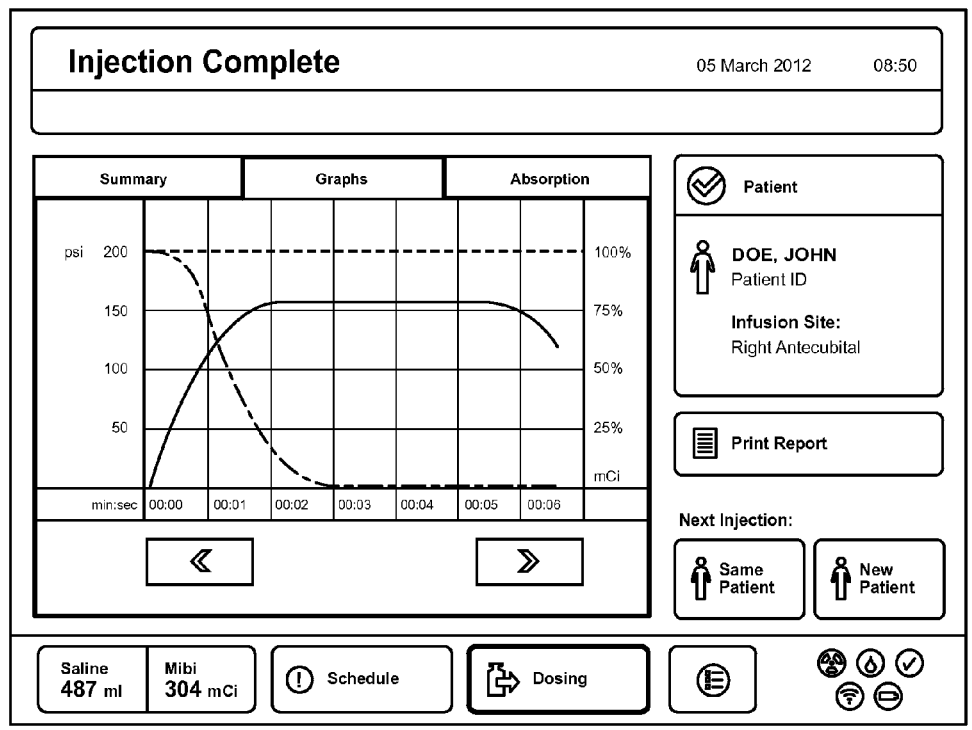
FIG. 34 is screen shot representing an exemplary window upon completion of the dosing protocol showing graphs produced during the dosing protocol.
Figure 35:
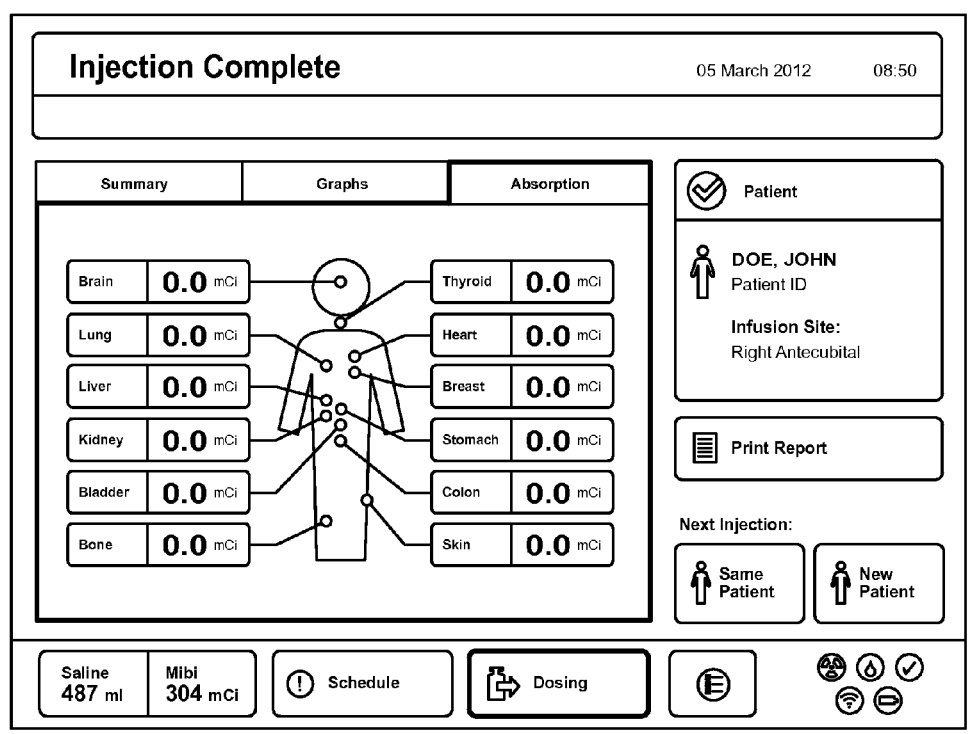
FIG. 35 is screen shot representing an exemplary window upon completion of the dosing protocol showing the relative amount of radiopharmaceutical that is absorbed by various organs.

This screen (FIG. 30) may further provide a means for tracking the injection and one or more button to inject the dose or discard the dose. Further information provided by the screen may include the injection rate, the amount of radiopharmaceutical to be injected based on the radioactive emissions of the radiopharmaceutical and the time remaining in the injection procedure. During the procedure, the delivery may be tracked based on the change in pressure of the system, and in some embodiments, delivery may be tracked based on the amount of radiopharmaceutical delivered based on, for example, the percent delivered or the percent remaining to be delivered as illustrated in FIG. 31. FIG. 32 show a screen shot showing the screen after injection is nearly complete. As illustrated in FIGS. 31 and 32, in some embodiments, pressure (psi) and the amount of radiopharmaceutical delivered based on, for example, activity of the radiopharmaceutical remaining in the coil, can be tracked simultaneously providing the user with immediate verification that the radiopharmaceutical is being delivered. The user may be alerted either audibly, visually, or both audibly and visually when the injection is completed. In some embodiments, a window may appear showing the results of the procedure. For example, as illustrated in FIG. 33, a window including a summary of the injection protocol may be provided that includes the volume and flow rate of the pharmaceutical agent and radiopharmaceutical delivered, and in some embodiments, the prescribed amount of radiopharmaceutical to be delivered, the actual amount of radiopharmaceutical delivered and the time of delivery. The total fluid delivered including both pharmaceuticals and saline or medical fluid may also be provided in the summary. In other embodiments windows providing the graphs produced during the procedure may be accessible after the procedure is complete as illustrated in FIG. 34, and yet another window may provide the relative amount of radiopharmaceutical that is absorbed by various organs as illustrated in FIG. 35. These data may generally represent the current rate of absorption for various organs. The screens provided in the FIG. 33-35 may further include a button for printing the individual reports or a compilation of the reports presented in each of the screens provided in FIG. 33-35. These screens may further include a button for transmitting the data and other information compiled during the procedure to a database such as hospital database systems such as a Picture Archiving Communication System (PACS), Hospital Information System (HIS), or Radiology Information System (RIS). Transmission of the data to these databases may be carried out via a wired or wireless Internet connection or wirelessly using, for example, Bluetooth. The screens may further include buttons for preparing the system for another injection either with the same patient or a new patient.

While the systems described above include a graphical display in the form of an x-y plot with the X-axis indicating the percent of the infusion that has been completed from 0 to 100 and the Y-axis indicating the percent of the dose that is remaining in the tube coil 410 from 0 to 100, this is not to be construed as limiting the present disclosure. For instance, various other values can be monitored against the percent of the dose remaining in the tube coil 410 to provide the operator with an indication of the status of the injection procedure such as, but not limited to, time, the percent of saline that has been injected, flow rate of saline or FDG, volume of saline or FDG injected, etc. In addition, the graphical display is not limited to an x-y plot and various other 1-dimensional and 2-dimensional graphical indications of the status of the injection procedure may be provided. For instance, the graphical representation may be a numeric display, a bar graph, or a scatter plot. In addition, the graphical representation may be a graphical display of vial 902 which is shown emptying as the injection procedure occurs.

Figure 36:
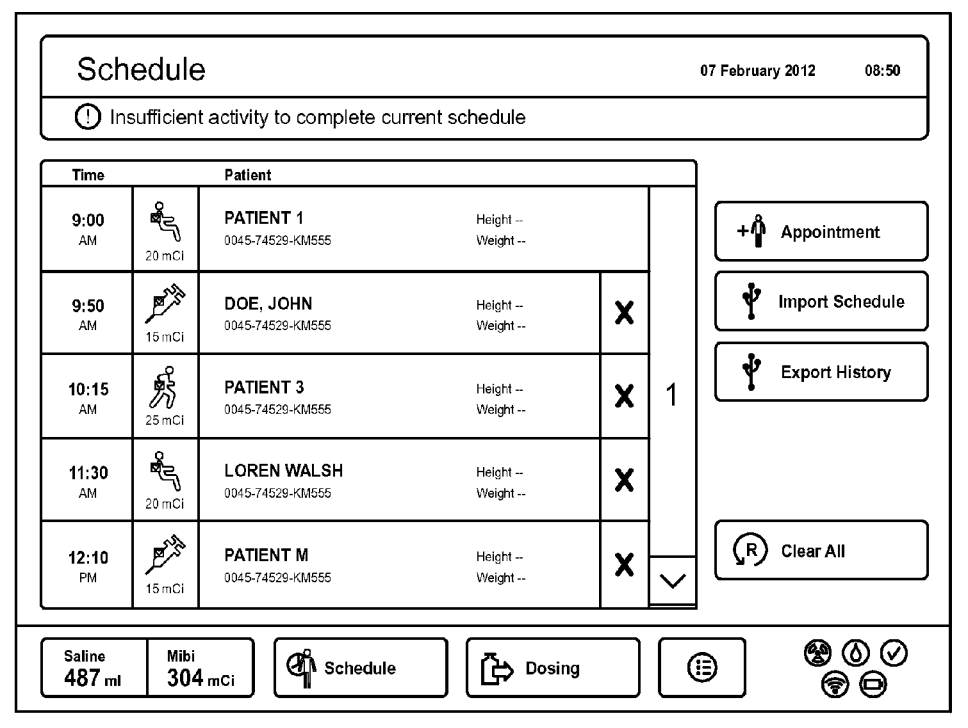

As illustrated in FIG. 36, the schedule screen may further include buttons to add an appointment or individual buttons to remove a patient from the list, presented as an "X" in the list provided in FIG. 36. Further buttons may allow for the schedule to be imported or exported. Importing and exporting can be carried out using a hard wired or wireless network or Internet, or secondary storage devices may be used to transfer patient data onto or off of the computer associated with the system. In other embodiments, patient information may be uploaded after a barcode associated with the patient has been scanned. In still further embodiments, the screen may include a button for saving data and/or clearing the entire patient list. In certain embodiments, the patient list may be interactive. For example, the list may allow for individual patient entries to be clicked on and the screen may provide information regarding the sufficiency of the patient data entered. In the event that one or more required fields have not been completed, the screen may prompt the user to add the data by indicating that insufficient data is provided or indicate which fields need to be completed before the procedure can be initiated.

Figure 37:
FIG. 37 is screen shot representing an exemplary window showing the tracking of the amount of saline and radiopharmaceutical delivered in real time.

In some embodiments, such as those illustrated in FIG. 37, the system may track the amount of saline and radiopharmaceutical in the system. As illustrated in FIG. 37, one or more windows may be provided that show the amount of saline and radiopharmaceutical remaining in real time. In some embodiments, the system may warn the user when insufficient radiopharmaceutical remains in the system to complete the schedule. In such cases, the list may be modified to indicate which procedures can be completed and those that cannot. For example, in FIG. 37, insufficient radiopharmaceutical is provided in the system to complete the scheduled procedure for Casey Joslin, but the previous procedures can be completed.

Figure 38:
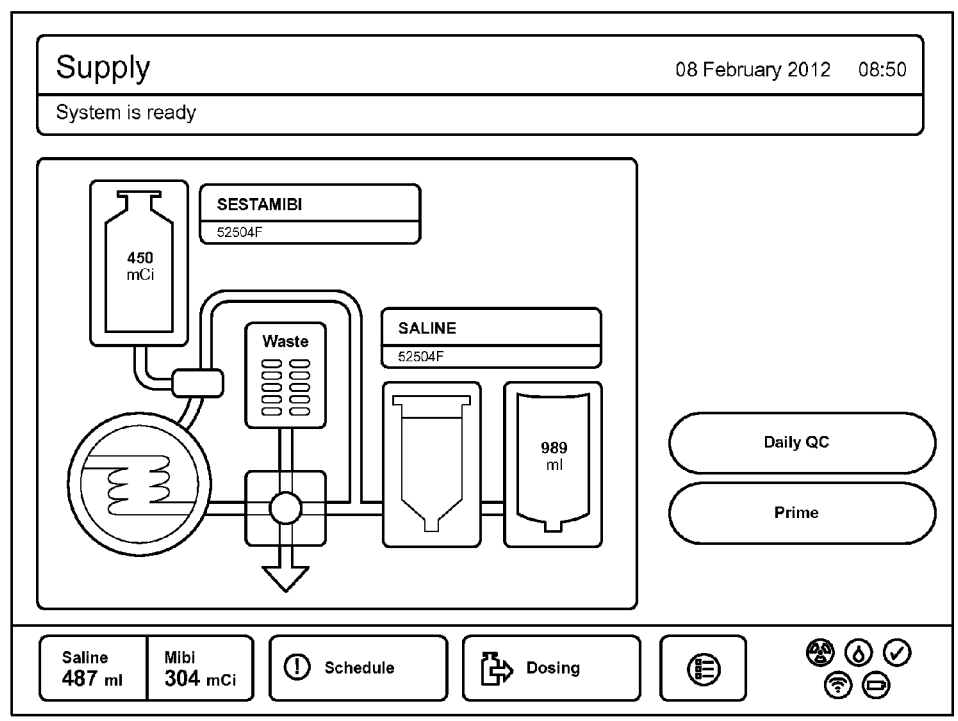
FIG. 38 is screen shot representing an exemplary window showing the amount of materials remaining in the system and the amount of waste in the waste receptacle.
Figure 39:
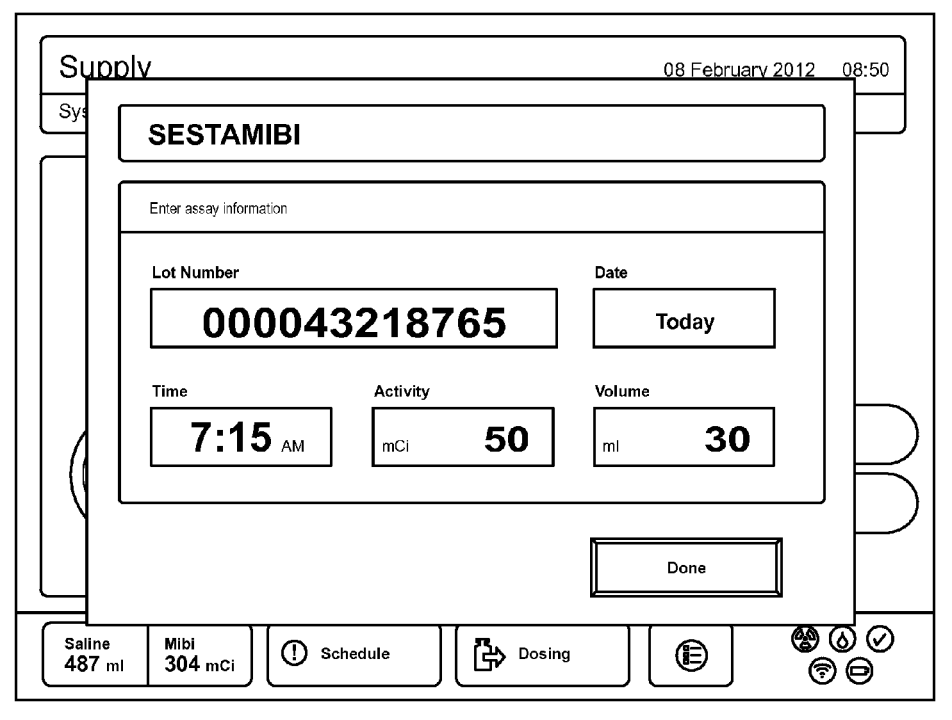
Figure 40:
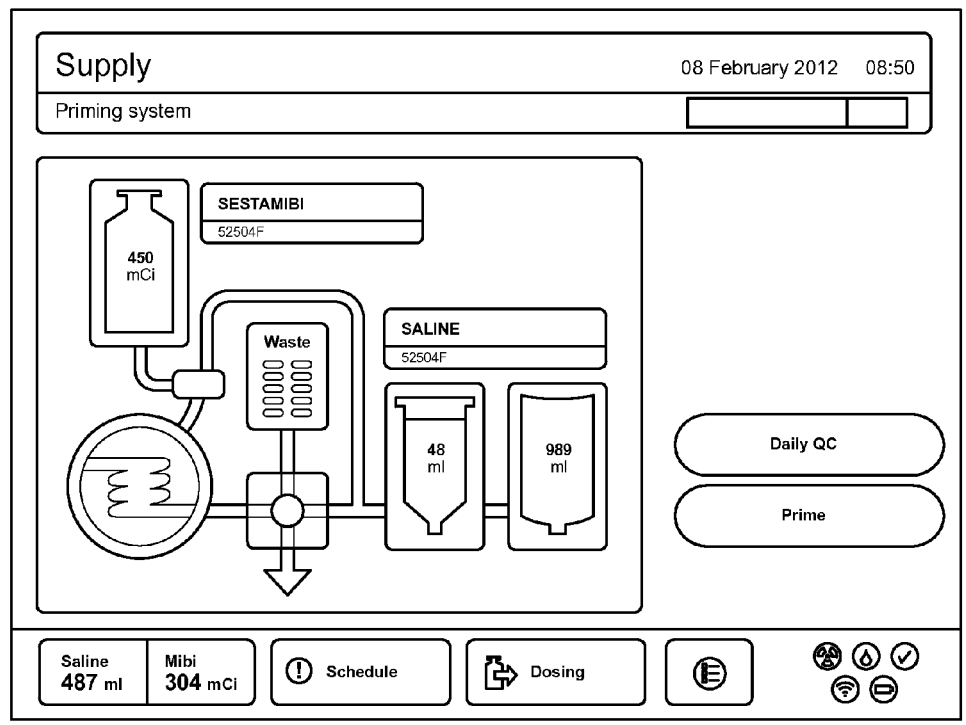
FIG. 40 is screen shot representing an exemplary window showing the progress of the priming protocol.
Figure 41:
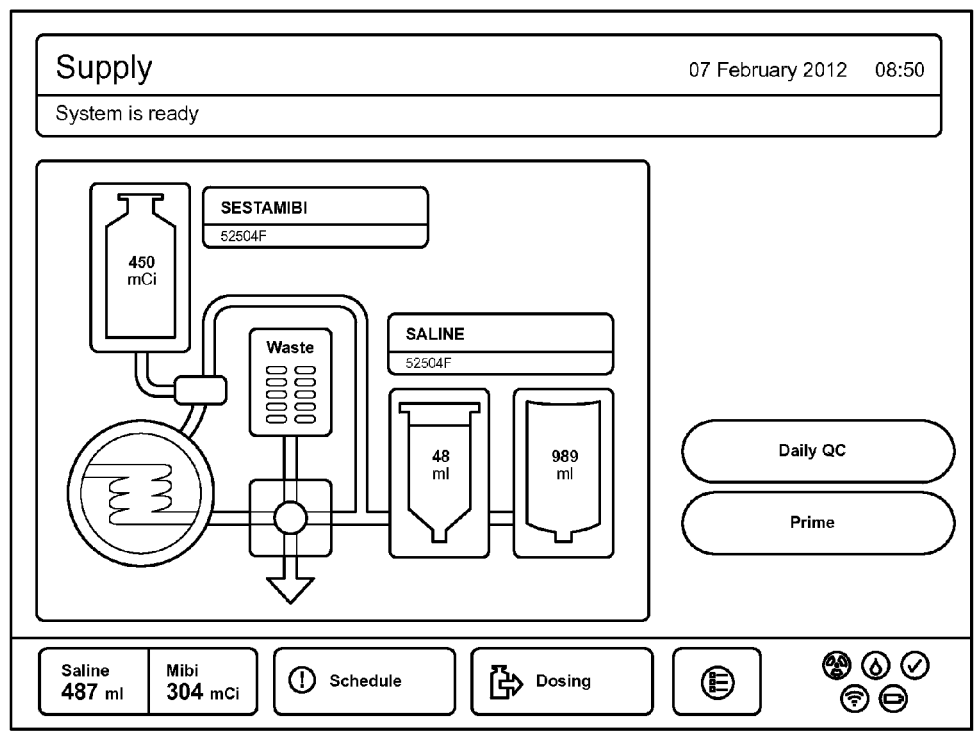
FIG. 41 is screen shot representing an exemplary window upon completion of the priming protocol.

In still other embodiments, a graphical display of the system may be provided in one or more windows that shows the amount of materials, such as saline, radiopharmaceutical (Sestimibi), and therapeutic agent remaining in the system and the amount of waste in the waste receptacle as illustrated in FIG. 38. In some embodiments, this graphical display may be interactive, such that the user can select any component of the system and input, for example, the lot number of the fluid, the date added, the time, the activity, and the volume as illustrated in the pop-up window shown in FIG. 39. Once the components have been identified, the system may prompt the user to prime the system by providing a button for priming the system, and the screen may show the progress of the priming protocol using, for example, a progress bar as shown in FIG. 40 or the tube set graphically illustrated in the system may highlight the portions of the system that have been primed during the priming protocol. The system may indicate that the priming protocol is complete audibly or graphically. For example, as provided in FIG. 41, the graphical system display of the system may be completely highlighted indicating that every portion of the system is properly primed and an indication that the system is primed may be provided elsewhere on the screen.

The system of various embodiments may include any number of cords for powering the system using standard AC outlets, and in some embodiments, the system may include a battery configured to power to the system controller and to the ionization/calibration chamber 310 in the event that the system 10 is disconnected from an AC power source. In some embodiments, the system battery may be charged while the system 10 is connected to an AC power source.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

The invention claimed is:

1. A fluid path set for use in a fluid delivery system, the fluid path set comprising:
   a confluence valve;
   a four-way valve;
   a first tubing section in fluid communication with a first input and the confluence valve;
   a second tubing section in fluid communication with a second input and the confluence valve;
   a third tubing section in fluid communication with the confluence valve and the four-way valve;
   an output tubing section in fluid communication with the four-way valve and at least one output fitting;
   a waste tubing section in fluid communication with the four-way valve and at least one waste receptacle; and
   an auxiliary tubing section in fluid communication with the four-way valve and the confluence valve.

2. The fluid path set of claim 1, further comprising a coil assembly disposed between the confluence valve and the four-way valve in fluid communication with at least the third tubing section.

3. The fluid path set of claim 1, further comprising a medical fluid storage container coupled to the first input.

4. The fluid path set of claim 3, wherein the medical fluid storage container comprises a cylindrical device having a plunger slidably inserted into the medical fluid storage container creating a seal.

5. The fluid path set of claim 3, further comprising a connector configured to connect to a fluid reservoir in fluid communication with the medical fluid storage container.

6. The fluid path set of claim 1, wherein the second input comprises a vial spike.

7. The fluid path set of claim 1, further comprising a pharmaceutical delivery port in fluid communication with the output tubing section.

8. The fluid path set of claim 1, wherein the at least one waste receptacle comprises an IV bag.

9. The fluid path set of claim 1, further comprising one or more of joints, linear joints, T-joints, 4-way joints, valves, check valves, by-pass valves, stop cocks, linkers, luer linkers, screw-type linkers, pressure fittings, and combinations thereof.

10. The fluid path set of claim 1, wherein each of the first tubing section, the second tubing section, the third tubing section, the output tubing section, the waste tubing section, and the auxiliary tubing section are permanently attached to at least one of the confluence valve and the four-way valve.

11. The fluid path set of claim 1, wherein the first input, the second input, the output fitting, or combinations thereof comprise a swabable valve.

12. The fluid path set of claim 1, further comprising:
   a portable tray operably coupled to the fluid path set, wherein the portable tray is configured to hold and separate components of the fluid path set.

13. The fluid path set of claim 12, wherein the portable tray comprises a rigid material.

14. The fluid path set of claim 12, wherein the portable tray comprises multiple grooves designed and configured to accept one or more of the first tubing section, the second tubing section, the third tubing section, the output tubing section, the waste tubing section, and the auxiliary tubing section.

15. The fluid path set of claim 12, wherein the portable tray comprises one or more openings.

16. The fluid path set of claim 12, wherein the portable tray comprises a vial spike permanently attached to a portion of the portable tray.

17. A portable fluid path set tray comprising:
   an upper side and a lower side;
   multiple grooves on the upper side designed and configured to accept and separate components of a fluid path set, wherein the components of the fluid path set comprise a first tubing section, a second tubing section, a third tubing section, an output tubing section, a waste tubing section, and an auxiliary tubing section; and
   a vial spike permanently attached to the tray.

18. The portable fluid path set tray of claim 17, wherein the tray comprises a rigid material.

19. The portable fluid path set tray of claim 17, further comprising one or more handles.

20. The fluid path set of claim 2, wherein the coil assembly comprises a tubing section formed in a helical coil of between about 5 and about 7 turns of a portion of the third tubing section.

21. The fluid path set of claim 20, wherein the coil assembly further comprises a core structure around which the helical coil is formed, the core structure comprising an upper shoulder and a lower shoulder that define a tube channel therebetween, the upper and lower shoulders adapted to retain the helical coil therebetween within the tube channel.

22. The portable fluid path set tray of claim 17, wherein the tray further comprises grooves or openings designed and configured to accept a confluence valve and a four-way valve, wherein the confluence valve is in fluid communication with the first tubing section, the second tubing section, and the third tubing section, and wherein the four-way valve is in fluid communication with the third tubing section, the output tubing section, the waste tubing section, and the auxiliary tubing section.

23. A sterile fluid delivery kit comprising:
   a fluid path set including:
      a confluence valve, a four-way valve,
a first tubing section in fluid communication with a first input and the confluence valve,
a second tubing section in fluid communication with a second input and the confluence valve,
a third tubing section in fluid communication with the confluence valve and the four-way valve,
an output tubing section in fluid communication with the four-way valve and at least one output fitting,
a waste tubing section in fluid communication with the four-way valve and at least one waste receptacle, and
an auxiliary tubing section in fluid communication with the four-way valve and the confluence valve;
a portable fluid path set tray composed of a rigid material and operably coupled to the fluid path set, wherein the fluid path set tray comprises:
an upper side and a lower side,
multiple grooves on the upper side designed and configured to accept and separate components of the fluid path set, and
a vial spike permanently attached to the portable fluid path set tray; and
a package defining an interior space adapted to house the fluid path set and the portable fluid path set tray,
wherein the interior space of the package, the fluid path set, and the portable fluid path set tray are sterile.

24. The sterile delivery kit of claim 23, wherein the portable fluid path set tray further comprises:
a medical fluid storage container coupled to the first input; and
a coil assembly disposed between the confluence valve and the four-way valve in fluid communication with at least the third tubing section.

* * * * *

UNITED STATES PATENT AND TRADEMARK OFFICE
CERTIFICATE OF CORRECTION

PATENT NO. : 9,039,592 B2
APPLICATION NO. : 13/828987
DATED : May 26, 2015
INVENTOR(S) : Kaintz et al.

Page 1 of 1

It is certified that error appears in the above-identified patent and that said Letters Patent is hereby corrected as shown below:

IN THE SPECIFICATION:

In Column 10, Line 26, delete "body 10" and insert -- body 11 --, therefor.
In Column 10, Line 28, delete "body 10" and insert -- body 11 --, therefor.
In Column 12, Line 16, delete "internal stem 2102" and insert -- internal stem 2101 --, therefor.
In Column 12, Line 17, delete "stem 2102 to" and insert -- stem 2101 to --, therefor.
In Column 12, Line 62, delete "waste tubing section 314" and insert -- waste tubing section 312 --, therefor.
In Columns 16 & 17, Lines 67 & 1, delete "waste tubing section 314" and insert -- waste tubing section 312 --, therefor.
In Column 23, Lines 12-13, delete "In-ocetreotide," and insert -- In-octreotide, --, therefor.
In Column 23, Line 27, delete "bood" and insert -- blood --, therefor.
In Column 23, Line 28, delete "$^{99m}$-sestamibi" and insert -- $^{99m}$Tc-sestamibi --, therefor.
In Column 25, Line 39, delete "than" and insert -- then --, therefor.

Signed and Sealed this
Twenty-ninth Day of December, 2015

Michelle K. Lee
*Director of the United States Patent and Trademark Office*